(12) United States Patent
Fujii et al.

(10) Patent No.: US 8,883,824 B2
(45) Date of Patent: Nov. 11, 2014

(54) 3-(4-AMINOPHENYL)-2-FURANCARBOXYLIC ACID DERIVATIVE AND PHARMACEUTICALLY ACCEPTABLE SALT THEREOF

(75) Inventors: Akihito Fujii, Osaka (JP); Kazumi Niidome, Suita (JP); Chiaki Migihashi, Osaka (JP); Toshiyuki Kamei, Yamatokoriyama (JP); Takafumi Matsumoto, Osaka (JP); Tomoyuki Hirata, Osaka (JP)

(73) Assignee: Sumitomo Dainippon Pharma Co., Ltd., Osaka (JP)

(*) Notice: Subject to any disclaimer, the term of this patent is extended or adjusted under 35 U.S.C. 154(b) by 312 days.

(21) Appl. No.: 13/320,204
(22) PCT Filed: May 12, 2010
(86) PCT No.: PCT/JP2010/058014
§ 371 (c)(1), (2), (4) Date: Nov. 11, 2011
(87) PCT Pub. No.: WO2010/131669
PCT Pub. Date: Nov. 18, 2010

(65) Prior Publication Data
US 2012/0059012 A1 Mar. 8, 2012

(30) Foreign Application Priority Data

May 14, 2009 (JP) ................................. 2009-118080

(51) Int. Cl.
| A61K 31/34 | (2006.01) |
| A61K 31/381 | (2006.01) |
| C07D 307/46 | (2006.01) |
| C07D 407/00 | (2006.01) |
| C07D 307/68 | (2006.01) |
| A61K 31/343 | (2006.01) |
| C07D 307/79 | (2006.01) |
| C07D 333/58 | (2006.01) |
| A61K 31/341 | (2006.01) |
| A61K 31/357 | (2006.01) |
| A61K 31/427 | (2006.01) |
| C07D 407/12 | (2006.01) |
| C07D 409/12 | (2006.01) |
| C07D 417/12 | (2006.01) |

(52) U.S. Cl.
CPC ............ *C07D 307/68* (2013.01); *A61K 31/343* (2013.01); *C07D 307/46* (2013.01); *C07D 307/79* (2013.01); *A61K 31/34* (2013.01); *C07D 333/58* (2013.01); *A61K 31/341* (2013.01); *A61K 31/357* (2013.01); *A61K 31/381* (2013.01); *A61K 31/427* (2013.01); *C07D 407/12* (2013.01); *C07D 409/12* (2013.01); *C07D 417/12* (2013.01)
USPC ........... 514/314; 514/336; 514/414; 514/471; 549/473; 549/487; 549/488

(58) Field of Classification Search
CPC ... A61K 31/343; A61K 31/34; A61K 31/341; A61K 31/357; A61K 31/427; C07D 307/68; C07D 307/46; C07D 307/79; C07D 407/12; C07D 409/12; C07D 417/12; C07D 333/58
USPC .......... 549/473, 487, 488; 514/314, 336, 414, 514/471
See application file for complete search history.

(56) References Cited

U.S. PATENT DOCUMENTS 7,514,452 B2 *   4/2009   Fujii et al. ..................... 514/314
2005/0171196 A1   8/2005   Fujii et al.

FOREIGN PATENT DOCUMENTS

JP    2005-60385 A    3/2005
WO   03/064404 A1    8/2003

OTHER PUBLICATIONS

Joslin's Diabetes Mellitus, 14th editioin, Joslin Diabetes Center, 2005, pp. 179-193.

(Continued)

*Primary Examiner* — Andrew D Kosar
*Assistant Examiner* — Raymond Covington
(74) *Attorney, Agent, or Firm* — Sughrue Mion, PLLC

(57) ABSTRACT

Disclosed is a compound represented by Formula (I) or a pharmaceutically acceptable salt thereof:

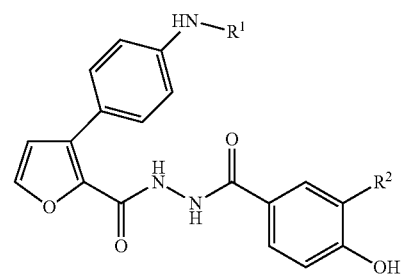

wherein $R^1$ is
1: a $C_{3-8}$ cycloalkyl $C_{1-4}$ alkyl group,
2: a $C_{7-14}$ aralkyl group, in which the aryl moiety thereof is optionally substituted with the same or different 1 to 3 groups selected from the group consisting of:
  (a) halogen,
  (b) $C_{1-4}$ alkyl, which is optionally substituted with 1 to 3 fluorine atoms,
  (c) $C_{1-4}$ alkoxy, which is optionally substituted with 1 to 3 fluorine atoms, and
  (d) $C_{1-4}$ alkylcarbonyl, which is optionally substituted with $C_{1-4}$ alkoxy,
3: a five-to ten-membered heteroaryl-$C_{1-4}$ alkyl group, in which the heteroaryl moiety thereof is optionally substituted with the same or different 1 to 3 groups selected from the group consisting of:
  (a) halogen, and
  (b) $C_{1-4}$ alkyl, or
4: a $C_{6-10}$ aryl $C_{2-6}$ alkenyl group; and
$R^2$ is a cyano group or a nitro group.

24 Claims, 2 Drawing Sheets

(56) References Cited

OTHER PUBLICATIONS

K.F. Petersen and J.T. Sullivan, "Effects of a novel glucagon receptor antagonist (Bay 27-9955) on glucagon-stimulated glucose production in humans", Diabetologia, vol. 44, 2001, pp. 2018-2024.

M. Sorhede Winzell et al., "Glucagon receptor antagonism improves islet function in mice with insulin resistance induced by a high-fat diet", Diabetologia, vol. 50, 2007, pp. 1453-1462.

Jun Liu and Lu-yong Zhang, "Setting up the screening model for glucagon receptor antagonists", Chinese Journal of Clinical Pharmacology and Therapeutics, vol. 11, No. 10, 2006, pp. 1129-1132 with English Abstract.

* cited by examiner

Ve: medium
Example 69 (0.1 mg/kg)
Sita: sitagliptin (5 mg/kg)

Ve: medium

Example 69 (3 mg/kg; administered twice a day)

Met: metformin (100 mg/kg; administered twice a day)

Ve: medium

Example 69 (3 mg/kg; administered twice a day)

Pio: pioglitazone (1 mg/kg; administered once a day)

3-(4-AMINOPHENYL)-2-FURANCARBOXYLIC ACID DERIVATIVE AND PHARMACEUTICALLY ACCEPTABLE SALT THEREOF

CROSS REFERENCE TO RELATED APPLICATION

This application is a National Stage of International Application No. PCT/JP2010/058014 filed May 12, 2010, claiming priority based on Japanese Patent Application No. 2009-118080, filed May 14, 2009, the contents of all of which are incorporated herein by reference in their entirety.

TECHNICAL FIELD

The present invention relates to a novel 3-(4-aminophenyl)-2-furancarboxylic acid derivative having glucagon receptor antagonistic activity, and to a pharmaceutically acceptable salt thereof.

BACKGROUND ART

Diabetes is widely believed to be caused by abnormality in two hormones, that is, absolute or relative insulin deficiency and relative glucagon excess. Insulin deficiency results in defects in sugar utilization, whereas glucagon excess leads to excessive production of sugar. Both cases contribute to hyperglycemia of diabetic patients.

Accordingly, inhibition of glucagon action is a rational method for reducing the blood sugar level of diabetic patients. Theoretically, glucagon action can be inhibited by reducing glucagon levels in the blood or by antagonizing glucagon action in the liver. The former can be achieved by suppressing the production or secretion of glucagon from a cells, or by neutralizing glucagon in the circulating blood. The latter can be achieved by administration of an effective glucagon receptor antagonist (NPL 1). Various low-molecular-weight glucagon receptor antagonists have been proposed so far, and they are reportedly able to reduce the blood sugar level of diabetic animal models. However, no compounds have been clinically used until now, and the development of compounds with higher drug efficacy and safety has been expected. For example, compounds (BAY 27-9955: NPL 2; and NMC 25-0926: NPL 3) shown below are reported as glucagon receptor antagonists; however, none of them has a 2-furancarboxylic acid hydrazide structure; their structures are different from the structure of the compound of the present invention.

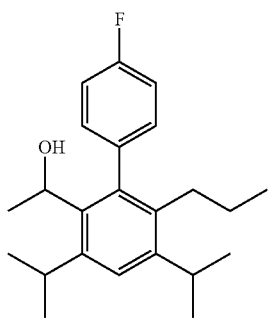

BAY 27-9955
((+)-isomer)

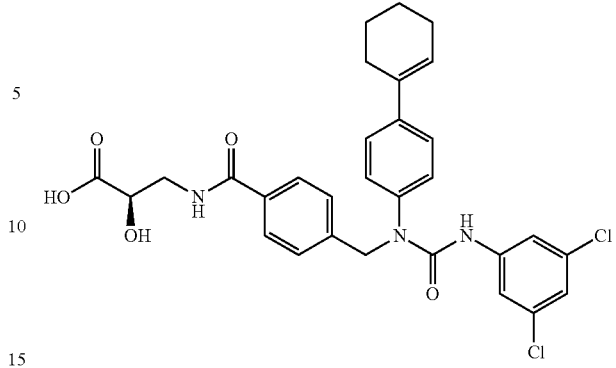

NNC 25-0926

In contrast, the following compound is referred to as an example of a compound having a 2-furancarboxylic acid hydrazide structure (PTL 1).

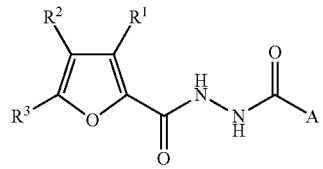

wherein A is a group represented by Formula (a) below:

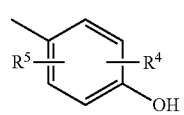

(a)

wherein either $R^4$ or $R^5$ is a cyano group, a nitro group, or the like, and the other is a hydrogen atom or a halogen atom,
or the like;
either $R^1$ or $R^2$ is a group: -D-(X)m-$R^6$, an aryl group, or the like, and the other is a group: -E-(Y)n-$R^7$, a hydrogen atom, an aryl group, or the like;
$R^3$ is a hydrogen atom, a halogen atom, or the like;
D and E are the same or different, and independently represent an arylene group;
X and Y are the same or different, and independently represent —O—, —S—, —SO—, —SO$_2$—, —OSO$_2$—, —NR$^8$—, —CO—, —CH=CH—, —C≡C—, —CONH—, —NHCO—, —NHCOO—, —OCH$_2$CONH—, or —OCH$_2$CO—;
$R^6$ and $R^7$ are the same or different, and independently represent a $C_{1-10}$ alkyl group, an aryl $C_{1-4}$ alkyl group, a heteroaryl $C_{1-4}$ alkyl group, or the like, with the alkyl moiety of the aryl $C_{1-4}$ alkyl group or heteroaryl $C_{1-4}$ alkyl group being optionally substituted with hydroxy;
$R^8$ is a hydrogen atom or a $C_{1-10}$ alkylcarbonyl group; and
m and n are independently 0 or 1;
provided that the aryl group, the aryl moiety, the heteroaryl group, the heteroaryl moiety, and the arylene group are optionally substituted with 1 to 4 atoms or groups selected from the group consisting of halogen, hydroxy, etc.

PTL 1 discloses a number of compounds in detail. However, only the following five compounds are disclosed as 2-furancarboxylic acid hydrazide derivatives having an aminophenyl group in position 3 of the furan ring.

Compound A

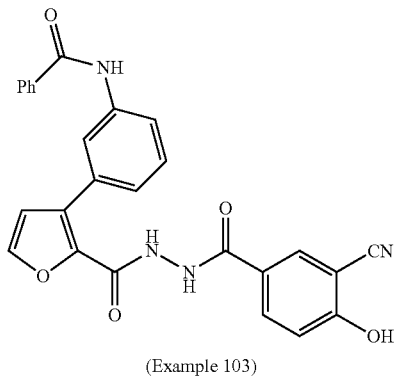

(Example 103)

Compound B

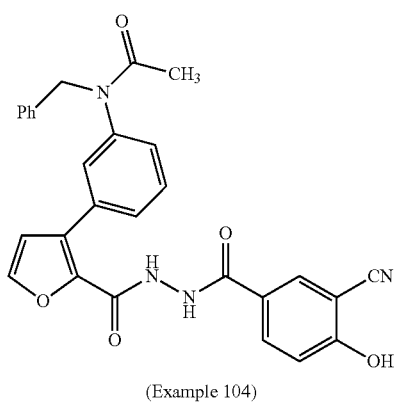

(Example 104)

Compound C

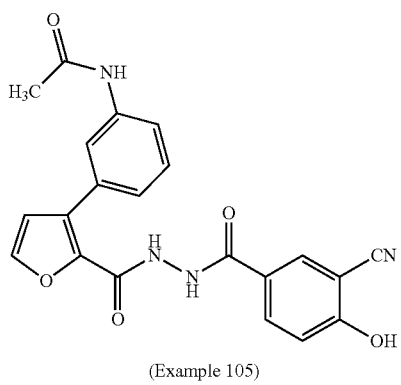

(Example 105)

Compound D

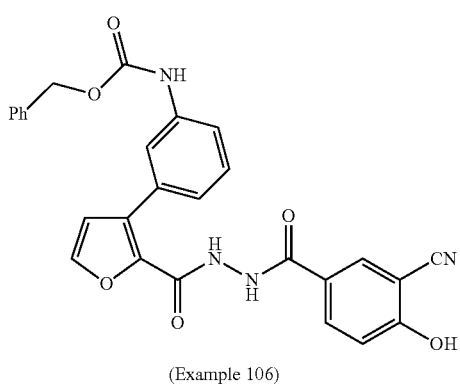

(Example 106)

Compound E

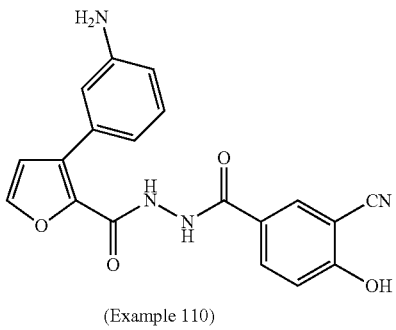

(Example 110)

These compounds (Compounds A to E) all have a 3-aminophenyl group as a partial structure. PTL 1 neither specifically discloses compounds having a 4-aminophenyl group as their partial structures, nor suggests their structures. In contrast, the glucagon receptor antagonistic activity of the 2-furancarboxylic acid hydrazide derivative disclosed in PTL 1 is not satisfactory at all. The creation of compounds having more potent antagonistic activity has been desired.

CITATION LIST

Patent Literature

PTL 1: WO 03/064404

Non-Patent Document

NPL 1: Joslin's Diabetes Mellitus, 14th edition, Joslin Diabetes Center, 2005, pp. 179-193
NPL 2: Diabetologia, 2001, vol. 44, pp. 2018-2024
NPL 3: Diabetologia, 2007, vol. 50, pp. 1453-1462

SUMMARY OF INVENTION

Technical Problem

Accordingly, the problem to be solved by the present invention is to find a compound having more potent antagonistic activity than existing compounds having glucagon receptor antagonistic activity. Another problem is to find an excellent therapeutic agent for diabetes based on such glucagon receptor antagonistic activity.

Solution to Problem

The present inventors have intensively studied related compounds of 2-furancarboxylic acid hydrazide derivatives, and surprisingly found that a 3-(4-aminophenyl)-2-furancarboxylic acid derivative has glucagon receptor antagonistic activity significantly superior to the prior art. More specifically, the present invention is as follows:

Item 1. A compound represented by Formula (I) or a pharmaceutically acceptable salt thereof:

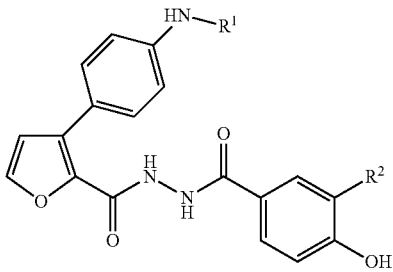

wherein $R^1$ is
1: a $C_{3-8}$ cycloalkyl $C_{1-4}$ alkyl group,
2: a $C_{7-14}$ aralkyl group, in which the aryl moiety thereof is optionally substituted with the same or different 1 to 3 groups selected from the group consisting of:
  (a) halogen,
  (b) $C_{1-4}$ alkyl, which is optionally substituted with 1 to 3 fluorine atoms,
  (c) $C_{1-4}$ alkoxy, which is optionally substituted with 1 to 3 fluorine atoms, and
  (d) $C_{1-4}$ alkylcarbonyl, which is optionally substituted with $C_{1-4}$ alkoxy,
3: a five- to ten-membered heteroaryl-$C_{1-4}$ alkyl group, in which the heteroaryl moiety thereof is optionally substituted with the same or different 1 to 3 groups selected from the group consisting of:
  (a) halogen, and
  (b) $C_{1-4}$ alkyl, or
4: a $C_{6-10}$ aryl $C_{2-6}$ alkenyl group; and
$R^2$ is a cyano group or a nitro group.

Item 2. The compound according to Item 1, or a pharmaceutically acceptable salt thereof, wherein $R^1$ is a $C_{7-14}$ aralkyl group, in which the aryl moiety thereof is substituted with the same or different 1 to 3 groups selected from the group consisting of:
  (a) halogen,
  (b) $C_{1-4}$ alkyl, which is optionally substituted with 1 to 3 fluorine atoms,
  (c) $C_{1-4}$ alkoxy, which is optionally substituted with 1 to 3 fluorine atoms, and
  (d) alkylcarbonyl, which is optionally substituted with $C_{1-4}$ alkoxy.

Item 3. The compound according to Item 1 or 2, or a pharmaceutically acceptable salt thereof, wherein $R^1$ is a $C_{7-14}$ aralkyl group, in which the aryl moiety thereof is substituted with alkyl optionally substituted with 1 to 3 fluorine atoms.

Item 4. The compound according to any one of Items 1 to 3, or a pharmaceutically acceptable salt thereof, wherein $R^1$ is a $C_{7-14}$ aralkyl group, in which the aryl moiety thereof is substituted with methyl, ethyl, 2-propyl, or 1,1,1-trimethylmethyl.

Item 5. The compound according to Item 1, or a pharmaceutically acceptable salt thereof, wherein $R^1$ is a 1-phenylethyl group, in which the phenyl moiety thereof is optionally substituted with the same or different 1 to 3 groups selected from the group consisting of:
  (a) halogen,
  (b) $C_{1-4}$ alkyl, which is optionally substituted with 1 to 3 fluorine atoms,
  (c) $C_{1-4}$ alkoxy, which is optionally substituted with 1 to 3 fluorine atoms, and
  (d) $C_{1-4}$ alkylcarbonyl, which is optionally substituted with $C_{1-4}$ alkoxy.

Item 6. The compound according to Item 5, or a pharmaceutically acceptable salt thereof, wherein $R^1$ is a 1-phenylethyl group, in which the phenyl moiety thereof is substituted with $C_{1-4}$ alkyl optionally substituted with 1 to 3 fluorine atoms.

Item 7. The compound according to Item 6, or a pharmaceutically acceptable salt thereof, wherein $R^1$ is a 1-phenylethyl group, in which the phenyl moiety thereof is substituted with methyl, ethyl, 2-propyl, or 1,1,1-trimethylmethyl.

Item 8. The compound according to Item 1, or a pharmaceutically acceptable salt thereof, wherein $R^1$ is a (1S)-1-phenylethyl group, in which the phenyl moiety thereof is optionally substituted with the same or different 1 to 3 groups selected from the group consisting of:
  (a) halogen,
  (b) $C_{1-4}$ alkyl, which is optionally substituted with 1 to 3 fluorine atoms,
  (c) $C_{1-4}$ alkoxy, which is optionally substituted with 1 to 3 fluorine atoms, and
  (d) $C_{1-4}$ alkylcarbonyl, which is optionally substituted with $C_{1-4}$ alkoxy.

Item 9. The compound according to Item 8, or a pharmaceutically acceptable salt thereof, wherein $R^1$ is a (1S)-1-phenylethyl group, in which the phenyl moiety thereof is substituted with $C_{1-4}$ alkyl optionally substituted with 1 to 3 fluorine atoms.

Item 10. The compound according to Item 9, or a pharmaceutically acceptable salt thereof, wherein $R^1$ is a (1S)-1-phenylethyl group, in which the phenyl moiety thereof is substituted with methyl, ethyl, 2-propyl, or 1,1,1-trimethylmethyl.

Item 11. The compound according to any one of Items 1 to 7, or a pharmaceutically acceptable salt thereof, wherein $R^1$ is a 1-(4-ethylphenyl)ethyl group.

Item 12. The compound according to any one of Items 1 to 7, or a pharmaceutically acceptable salt thereof, wherein $R^1$ is a 1-(4-ethylphenyl)ethyl group.

Item 13. The compound according to any one of Items 1 to 7, or a pharmaceutically acceptable salt thereof, wherein $R^1$ is a 1-(4-(2-propyl)phenyl)ethyl group.

Item 14. The compound according to any one of Items 1 to 7, or a pharmaceutically acceptable salt thereof, wherein $R^1$ is a 1-(4-(1,1,1-trimethylmethyl)phenyl)ethyl group.

Item 15. The compound according to Item 1, or a pharmaceutically acceptable salt thereof, wherein $R^1$ is a five- to ten-membered heteroaryl-$C_{1-4}$ alkyl group, in which the heteroaryl moiety thereof is substituted with the same or different 1 to 3 groups selected from the group consisting of:
  (a) halogen, and
  (b) $C_{1-4}$ alkyl.

Item 16. The compound according to any one of Items 1 to 15, or a pharmaceutically acceptable salt thereof, wherein $R^2$ is a cyano group.

Item 17. The compound according to any one of Items 1 to 15, or a pharmaceutically acceptable salt thereof, wherein $R^2$ is a nitro group.

Item 18. The compound according to Item 1 selected from a compound group below, or a pharmaceutically acceptable salt thereof, the compound group consisting of:
3-(4-{[1-(4-methylphenyl)ethyl]amino}phenyl)-2-furancarboxylic acid-2-(4-hydroxy-3-nitrobenzoyl)hydrazide, 3-[4-({1-[(2-propyl)phenyl]ethyl}amino)phenyl]-2-furancarboxylic acid-2-(4-hydroxy-3-nitrobenzoyl)hydrazide, 3-[4-({1-[(1,1-trimethylmethyl)phenyl]ethyl}amino)phenyl]-2-furancarboxylic acid-2-(4-hydroxy-3-nitrobenzoyl)hydrazide, 3-{4-[(1-phenylpropyl)amino]phenyl}-2-furancarboxylic acid-2-(4-hydroxy-3-nitrobenzoyl)hydrazide, 3-{4-[(1-phenylbutyl)amino]phenyl}-2-furancarboxylic acid-2-(4-hydroxy-3-nitrobenzoyl)hydrazide, 3-{4-[(1-phenylethyl)amino]phenyl}-2-furancarboxylic acid-2-(4-hydroxy-3-nitrobenzoyl)hydrazide, 3-(4-{[1-(2,4-dimethylphenyl)ethyl]amino}phenyl)-2-furancarboxylic acid-2-(4-hydroxy-3-nitrobenzoyl)hydrazide, 3-(4-{[1-(4-fluorophenyl)ethyl]amino}phenyl)-2-furancarboxylic acid-2-(4-hydroxy-3-nitrobenzoyl)hydrazide, 3-(4-{[1-(3-methylphenyl)ethyl]amino}phenyl)-2-furancarboxylic acid-2-(4-hydroxy-3-nitrobenzoyl)hydrazide, 3-(4-{[1-(4-ethylphenyl)ethyl]amino}phenyl)-2-furancarboxylic acid-2-(4-hydroxy-3-nitrobenzoyl)hydrazide, 3-(4-{[1-(3,4-difluorophenyl)ethyl]amino}phenyl)-2-furancarboxylic acid-2-(4-hydroxy-3-nitrobenzoyl)hydrazide, 3-(4-{[1-(2,4-difluorophenyl)ethyl]amino}phenyl)-2-furancarboxylic acid-2-(4-hydroxy-3-nitrobenzoyl)hydrazide, 3-(4-{[1-(1-benzofuran-2-yl)ethyl]amino}phenyl)-2-furancarboxylic acid-2-(4-hydroxy-3-nitrobenzoyl)hydrazide, 3-(4-{[1-(4-methoxyphenyl)propan-2-yl]amino}phenyl)-2-furancarboxylic acid-2-(4-hydroxy-3-nitrobenzoyl)hydrazide, 3-(4-{[1-(4-methylphenyl)propan-2-yl]amino}phenyl)-2-furancarboxylic acid-2-(4-hydroxy-3-nitrobenzoyl)hydrazide, 3-(4-{[1-(3,4,5-trifluorophenyl)ethyl]amino}phenyl)-2-furancarboxylic acid-2-(4-hydroxy-3-nitrobenzoyl)hydrazide, 3-(4-{[1-(4-fluoro-3-methoxyphenyl)ethyl]amino}phenyl)-2-furancarboxylic acid-2-(4-hydroxy-3-nitrobenzoyl)hydrazide, 3-(4-{[1-(4-bromo-2-fluorophenyl)ethyl]amino}phenyl)-2-furancarboxylic acid-2-(4-hydroxy-3-nitrobenzoyl)hydrazide, 3-(4-{[1-(4-bromophenyl)ethyl]amino}phenyl)-2-furancarboxylic acid-2-(4-hydroxy-3-nitrobenzoyl)hydrazide, 3-(4-{[4-(4-methoxyphenyl)butan-2-yl]amino}phenyl)-2-furancarboxylic acid-2-(4-hydroxy-3-nitrobenzoyl)hydrazide, 3-(4-{[1-(3,4-dichlorophenyl)ethyl]amino}phenyl)-2-furancarboxylic acid-2-(4-hydroxy-3-nitrobenzoyl)hydrazide, 3-(4-{[1-(3-chlorophenyl)ethyl]amino}phenyl)-2-furancarboxylic acid-2-(4-hydroxy-3-nitrobenzoyl)hydrazide, 3-(4-{[1-(4-chlorophenyl)ethyl]amino}phenyl)-2-furancarboxylic acid-2-(4-hydroxy-3-nitrobenzoyl)hydrazide, 3-(4-{[1-(naphthalen-2-yl)ethyl]amino}phenyl)-2-furancarboxylic acid-2-(4-hydroxy-3-nitrobenzoyl)hydrazide, 3-(4-{[1-(3,4-dimethoxyphenyl)ethyl]amino}phenyl)-2-furancarboxylic acid-2-(4-hydroxy-3-nitrobenzoyl)hydrazide, 3-(4-{[1-(3-fluoro-4-methoxyphenyl)ethyl]amino}phenyl)-2-furancarboxylic acid-2-(4-hydroxy-3-nitrobenzoyl)hydrazide, 3-(4-{[1-(4-propylphenyl)ethyl]amino}phenyl)-2-furancarboxylic acid-2-(4-hydroxy-3-nitrobenzoyl)hydrazide, 3-(4-{[1-(4-trifluoromethoxyphenyl)ethyl]amino}phenyl)-2-furancarboxylic acid-2-(4-hydroxy-3-nitrobenzoyl)hydrazide, 3-{4-[(4-phenylbutan-2-yl)amino]phenyl}-2-furancarboxylic acid-2-(4-hydroxy-3-nitrobenzoyl)hydrazide, 3-(4-{[1-(4-chlorophenyl)propan-2-yl]amino}phenyl)-2-furancarboxylic acid-2-(4-hydroxy-3-nitrobenzoyl)hydrazide, 3-(4-{[1-(naphthalen-1-yl)ethyl]amino}phenyl)-2-furancarboxylic acid-2-(4-hydroxy-3-nitrobenzoyl)hydrazide, 3-(4-{[1-(3-chloro-4-fluorophenyl)ethyl]amino}phenyl)-2-furancarboxylic acid-2-(4-hydroxy-3-nitrobenzoyl)hydrazide, 3-(4-{[1-(3-chlorophenyl)ethyl]amino}phenyl)-2-furancarboxylic acid-2-(4-hydroxy-3-nitrobenzoyl)hydrazide, 3-[4-({1-[4-(methoxyacetyl)phenyl]ethyl}amino)phenyl]-2-furancarboxylic acid-2-(4-hydroxy-3-nitrobenzoyl)hydrazide, 3-(4-{[1-(4-trifluoromethylphenyl)ethyl]amino}phenyl)-2-furancarboxylic acid-2-(4-hydroxy-3-nitrobenzoyl)hydrazide, 3-(4-{[(3E)-4-phenylbut-3-en-2-yl]amino}phenyl)-2-furancarboxylic acid-2-(4-hydroxy-3-nitrobenzoyl)hydrazide, 3-(4-{[1-(4-fluoronaphthalen-1-yl)ethyl]amino}phenyl)-2-furancarboxylic acid-2-(4-hydroxy-3-nitrobenzoyl)hydrazide, 3-(4-{[1-(4-methoxyphenyl)ethyl]amino}phenyl)-2-furancarboxylic acid-2-(4-hydroxy-3-nitrobenzoyl)hydrazide, 3-(4-{[1-(3-chloro-4-methoxyphenyl)ethyl]amino}phenyl)-2-furancarboxylic acid-2-(4-hydroxy-3-nitrobenzoyl)hydrazide, 3-(4-{[1-(2,3,4-trifluorophenyl)ethyl]amino}phenyl)-2-furancarboxylic acid-2-(4-hydroxy-3-nitrobenzoyl)hydrazide, 3-(4-{[1-(6-methylnaphthalen-2-yl)ethyl]amino}phenyl)-2-furancarboxylic acid-2-(4-hydroxy-3-nitrobenzoyl)hydrazide, 3-(4-{[1-(4-fluoro-2-methoxyphenyl)ethyl]amino}phenyl)-2-furancarboxylic acid-2-(4-hydroxy-3-nitrobenzoyl)hydrazide, 3-(4-{[1-(1-benzothiophen-3-yl)ethyl]amino}phenyl)-2-furancarboxylic acid-2-(4-hydroxy-3-nitrobenzoyl)hydrazide, 3-(4-{[1-(3,4-dimethylphenyl)ethyl]amino}phenyl)-2-furancarboxylic acid-2-(4-hydroxy-3-nitrobenzoyl)hydrazide, 3-(4-{[1-(2-chloro-4-fluorophenyl)ethyl]amino}phenyl)-2-furancarboxylic acid-2-(4-hydroxy-3-nitrobenzoyl)hydrazide, 3-(4-{[1-(4-chloro-3-methylphenyl)ethyl]amino}phenyl)-2-furancarboxylic acid-2-(4-hydroxy-3-nitrobenzoyl)hydrazide, 3-(4-{[1-(3-fluoro-4-methylphenyl)ethyl]amino}phenyl)-2-furancarboxylic acid-2-(4-hydroxy-3-nitrobenzoyl)hydrazide, 3-(4-{[1-(2,3-difluoro-4-methylphenyl)ethyl]amino}phenyl)-2-furancarboxylic acid-2-(4-hydroxy-3-nitrobenzoyl)hydrazide, 3-(4-{[1-(4-chloro-2-fluorophenyl)ethyl]amino}phenyl)-2-furancarboxylic acid-2-(4-hydroxy-3-nitrobenzoyl)hydrazide, 3-(4-{[(1S)-1-(4-fluorophenyl)ethyl]amino}phenyl)-2-furancarboxylic acid-2-(4-hydroxy-3-nitrobenzoyl)hydrazide, and 3-(4-{[(1S)-1-(4-methylphenyl)ethyl]amino}phenyl)-2-furancarboxylic acid-2-(4-hydroxy-3-nitrobenzoyl)hydrazide.

Item 19. The compound according to Item 1 selected from a compound group below, or a pharmaceutically acceptable salt thereof, the compound group consisting of:

3-(4-{[1-(4-methylphenyl)ethyl]amino}phenyl)-2-furancarboxylic acid-2-(4-hydroxy-3-nitrobenzoyl)hydrazide, 3-(4-{[(1-phenylethyl)amino]phenyl}-2-furancarboxylic acid-2-(4-hydroxy-3-nitrobenzoyl)hydrazide, 3-(4-{[1-(4-fluorophenyl)ethyl]amino}phenyl)-2-furancarboxylic acid-2-(4-hydroxy-3-nitrobenzoyl)hydrazide, 3-(4-{[1-(4-ethylphenyl)ethyl]amino}phenyl)-2-furancarboxylic acid-2-(4-hydroxy-3-nitrobenzoyl)hydrazide, 3-(4-{[1-(4-chlorophenyl)ethyl]amino}phenyl)-2-furancarboxylic acid-2-(4-hydroxy-3-nitrobenzoyl)hydrazide, 3-(4-{[1-(3,4-dimethylphenyl)ethyl]amino}phenyl)-2-furancarboxylic acid-2-(4-hydroxy-3-nitrobenzoyl)hydrazide, 3-(4-{[1-(4-chloro-3-methylphenyl)ethyl]amino}phenyl)-2-furancarboxylic acid-2-(4-hydroxy-3-nitrobenzoyl)hydrazide, 3-(4-{[1-(4-chloro-2-fluorophenyl)ethyl]amino}phenyl)-2-furancarboxylic acid-2-(4-hydroxy-3-nitrobenzoyl)hydrazide, and 3-(4-{[1(1S)-1-(4-methylphenyl)ethyl]amino}phenyl)-2-furancarboxylic acid-2-(4-hydroxy-3-nitrobenzoyl)hydrazide.

Item 20. A compound represented by Formula (II) or a pharmaceutically acceptable salt thereof:

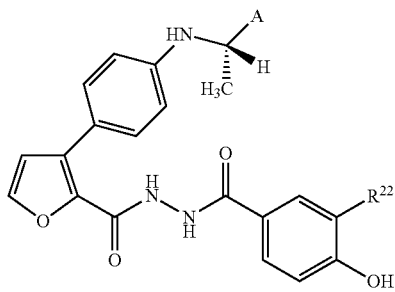

(II)

wherein A is one member selected from the groups represented by Formulae (a) to (d) below:

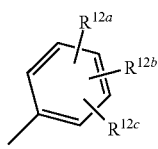

(a)

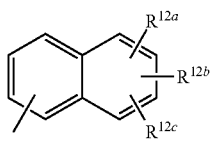

(b)

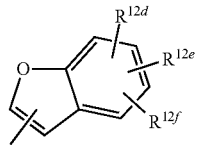

(c)

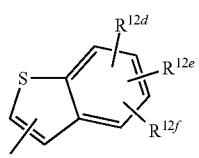

(d)

wherein $R^{12a}$, $R^{12b}$, and $R^{12c}$ are the same or different, and independently represent:
1: a hydrogen atom,
2: a halogen atom,
3: a $C_{1-4}$ alkyl group, which is optionally substituted with 1 to 3 fluorine atoms,
4: a $C_{1-4}$ alkoxy group, which is optionally substituted with 1 to 3 fluorine atoms, or
5: a $C_{1-4}$ alkylcarbonyl group, which is optionally substituted with $C_{1-4}$ alkoxy;

$R^{12d}$, $R^{12e}$, and $R^{12f}$ are the same or different, and independently represent:
1: a hydrogen atom,
2: a halogen atom, or
3: $C_{1-4}$ alkyl; and $R^{22}$ is a cyano group or a nitro group.

Item 21. The compound according to Item 20, or a pharmaceutically acceptable salt thereof, wherein A is represented by Formula (a) below:

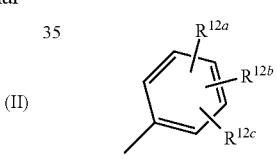

(a)

Item 22. The compound according to Item 20 or 21, or a pharmaceutically acceptable salt thereof, wherein $R^{22}$ is a nitro group.

Item 23. A compound represented by Formula (III) or a pharmaceutically acceptable salt thereof:

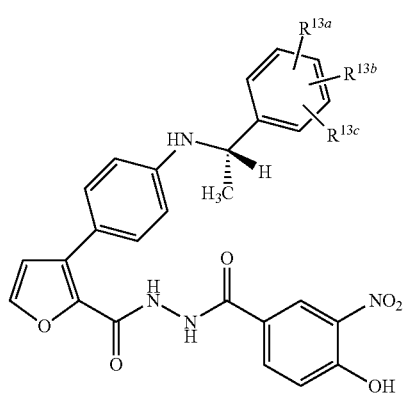

(III)

wherein $R^{13a}$, $R^{13b}$ and $R^{13c}$ are the same or different, and independently represent:
1: a hydrogen atom,
2: a halogen atom,
3: a $C_{1-4}$ alkyl group, which is optionally substituted with 1 to 3 fluorine atoms, 4: a $C_{1-4}$ alkoxy group, which is optionally substituted with 1 to 3 fluorine atoms, or 5: a $C_{1-4}$ alkylcarbonyl group, which is optionally substituted with $C_{1-4}$ alkoxy.

Item 24. A pharmaceutical composition comprising the compound according to any one of Items 1 to 23 or a pharmaceutically acceptable salt thereof.

Item 25. A pharmaceutical composition comprising the compound according to any one of Items 1 to 23 or a pharmaceutically acceptable salt thereof for use in prevention and/or treatment of a symptom and disease selected from the group consisting of hyperglycemia, abnormal glucose tolerance, insulin resistance syndrome, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, metabolic syndrome, and diabetic complications.

Item 26. A therapeutic agent for diabetes comprising the compound according to any one of Items 1 to 23 or a pharmaceutically acceptable salt thereof.

Item 27. A method for treating and/or preventing a symptom and disease selected from the group consisting of hyperglycemia, abnormal glucose tolerance, insulin resistance syndrome, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, metabolic syndrome, and diabetic complications; the method comprising administering an effective amount of the compound according to any one of Items 1 to 23 or a pharmaceutically acceptable salt thereof as an active ingredient into a patient.

Item 28. Use of the compound according to any one of Items 1 to 23 or a pharmaceutically acceptable salt thereof to prepare a pharmaceutical composition for preventing and/or treating a symptom and disease selected from the group consisting of hyperglycemia, abnormal glucose tolerance, insulin resistance syndrome, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, metabolic syndrome, and diabetic complications.

Item 29. A pharmaceutical comprising a combination of the compound according to any one of Items 1 to 23 or a pharmaceutically acceptable salt thereof and one drug selected from a drug group (A) below;

the drug group (A) consisting of insulin preparations, insulin resistance improving agents, α-glucosidase inhibitors, biguanides, insulin secretagogues, GLP-1, GLP-1 analogs, GLP-1 secretagogues, protein tyrosine phosphatase inhibitors, β3-agonists, DPPIV inhibitors, amyrin agonists, gluconeogenesis inhibitors, SGLT (sodium-glucose cotransporter) inhibitors, 11β-HSD1 inhibitors, adiponectin or adiponectin receptor agonists, leptin resistance improving drugs, somatostatin receptor agonists, AMPK activators, aldose reductase inhibitors, neurotrophic factors, PKC inhibitors, AGE inhibitors, active oxygen-eliminating agents, cerebral vasodilators, HMG-CoA reductase inhibitors, squalene synthetase inhibitors, ACAT inhibitors, cholesterol absorption inhibitors, angiotensin-converting enzyme inhibitors, angiotensin II antagonists, calcium antagonists, ACE/NEP inhibitors, β-blockers, α-blockers, αβ-blockers, renin inhibitors, aldosterone receptor antagonists, central anti-obesity drugs, pancreatic lipase inhibitors, peptide appetite suppressants, cholecystokinin agonists, xanthine derivatives, thiazide preparations, anti-aldosterone preparations, carbonic anhydrase inhibitors, chlorobenzene sulfonamide preparations, azosemido, isosorbide, ethacrynic acid, piretanide, bumetanide, and furosemide.

Item 30. A pharmaceutical comprising the combination according to Item 29, wherein the drug group (A) consists of insulin preparations, insulin resistance improving agents, α-glucosidase inhibitors, biguanides, insulin secretagogues, DPPIV inhibitors, GLP-1, GLP-1 analogs, and GLP-1 secretagogues.

Item 31. A method for treating and/or preventing a symptom and disease selected from the group consisting of hyperglycemia, abnormal glucose tolerance, insulin resistance syndrome, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, metabolic syndrome, and diabetic complications; the method comprising administering the compound according to any one of Items 1 to 23 or a pharmaceutically acceptable salt thereof, and one drug selected from the drug group (A) defined in Item 29 into a mammal.

Item 32. The treating and/or preventing method according to Item 31, wherein the drug group (A) consists of insulin preparations, insulin resistance improving agents, α-glucosidase inhibitors, biguanides, insulin secretagogues, DPPIV inhibitors, GLP-1, GLP-1 analogs, and GLP-1 secretagogues.

Item 33. Use of the compound according to any one of Items 1 to 23 or a pharmaceutically acceptable salt thereof, and one drug selected from the drug group (A) defined in Item 29 to prepare a pharmaceutical composition for preventing and/or treating a symptom and disease selected from the group consisting of hyperglycemia, abnormal glucose tolerance, insulin resistance syndrome, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, metabolic syndrome, and diabetic complications.

Item 34. The use according to Item 33, wherein the drug group (A) consists of insulin preparations, insulin resistance improving agents, α-glucosidase inhibitors, biguanides, insulin secretagogues, DPPIV inhibitors, GLP-1, GLP-1 analogs, and GLP-1 secretagogues.

Item 35. A method for producing a compound represented by Formula (I) or a pharmaceutically acceptable salt thereof:

(I)

wherein $R^1$ is

1: a $C_{3-8}$ cycloalkyl $C_{1-4}$ alkyl group,

2: a $C_{7-14}$ aralkyl group, in which the aryl moiety thereof is optionally substituted with the same or different 1 to 3 groups selected from the group consisting of:
  (a) halogen,
  (b) $C_{1-4}$ alkyl, which is optionally substituted with 1 to 3 fluorine atoms, (c) C$_{1-4}$ alkoxy, which is optionally substituted with 1 to 3 fluorine atoms, and
(d) C$_{1-4}$ alkylcarbonyl, which is optionally substituted with C$_{1-4}$ alkoxy,
3: a five- to ten-membered heteroaryl-C$_{1-4}$ alkyl group, in which the heteroaryl moiety thereof is optionally substituted with the same or different 1 to 3 groups selected from the group consisting of:
(a) halogen, and
(b) C$_{1-4}$ alkyl; or
4: a C$_{6-10}$ aryl C$_{2-6}$ alkenyl group; and
R$^2$ is a cyano group or a nitro group;
the method comprising steps 1 to 5 below:
Step 1: reacting a compound represented by Formula (A):

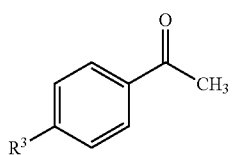
(A)

wherein R$^3$ is a halogen atom or a group: —N(R$^1$)(R$^5$), R$^5$ is a hydrogen atom, and R$^1$ is as defined above, with a compound represented by Formula (B):

HCOOR$^6$ (B)

wherein R$^6$ is a C$_{1-6}$ alkyl group, in the presence of a base, followed by a reaction in an alcohol solvent: R$^4$OH, wherein R$^4$ is a C$_{1-6}$ alkyl group, in the presence of an acid;
Step 2: reacting the compound obtained by the reaction of step 1 and represented by Formula (C):

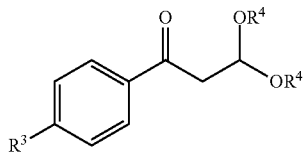
(C)

wherein R$^3$ and R$^4$ are as defined above, with a compound represented by Formula (E):

X$^1$—CH$_2$COOR$^7$ (E)

wherein X$^1$ is a halogen atom, and
R$^7$ is
1: a C$_{1-6}$ alkyl group,
2: a C$_{7-14}$ aralkyl group, which is optionally substituted with the same or different 1 to 3 groups selected from the group consisting of:
(a) halogen,
(b) methyl,
(c) methoxy, and
(e) nitro, or
3: a C$_{6-10}$ arylcarbonyl C$_{1-4}$ alkyl group, which is substituted with the same or different 1 to 3 groups selected from the group consisting of:
(a) halogen,
(b) methyl, and
(c) methoxy,
in the presence of a base;
Step 3: reacting the compound obtained by the reaction of step 2 and represented by Formula (F):

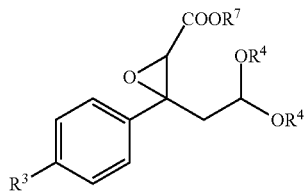
(F)

wherein R$^3$, R$^4$, and R$^7$ are as defined above, in the presence of an acid;
Step 4: reacting the compound obtained by the reaction of step 3 and represented by Formula (G):

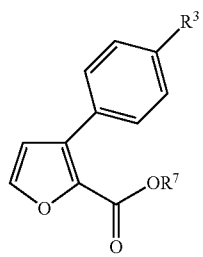
(G)

wherein R$^3$ and R$^7$ are as defined above, with
(1) hydrazine monohydrate after a coupling reaction with a compound represented by Formula (H) below, when R$^3$ is a halogen atom:

R$^1$NH$_2$ (H)

wherein R$^1$ is as defined above, or with
(2) hydrazine monohydrate, when R$^3$ is a group: —NH(R$^1$); and
step 5: reacting the compound obtained by the reaction of step 4 and represented by Formula (J):

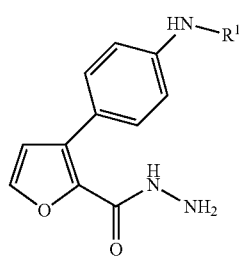
(J)

wherein R$^1$ is as defined above, with a compound represented by Formula (K):

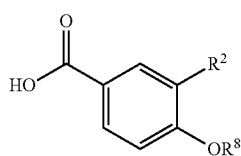
(K)

wherein R$^2$ is as defined above, and R$^8$ is a hydrogen atom, a C$_{1-4}$ alkyl group, a C$_{1-4}$ alkoxy C$_{1-4}$ alkyl group, a C$_{6-10}$ aryl group, a C$_{7-14}$ aralkyl group, or a C$_{1-4}$ alkylcarbonyl group; and, as necessary, converting the reaction product to a pharmaceutically acceptable salt.

Item 36. A compound represented by Formula (IV) below or a pharmaceutically acceptable salt thereof:

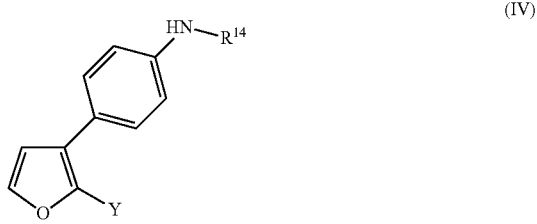

(IV)

wherein $R^{14}$ is

1: a $C_{3-8}$ cycloalkyl $C_{1-4}$ alkyl group,

2: a $C_{7-14}$ aralkyl group, in which the aryl moiety thereof is optionally substituted with the same or different 1 to 3 groups selected from the group consisting of:
  (a) halogen,
  (b) $C_{1-4}$ alkyl, which is optionally substituted with 1 to 3 fluorine atoms,
  (c) alkoxy, which is optionally substituted with 1 to 3 fluorine atoms, and
  (d) $C_{1-4}$ alkylcarbonyl, which is optionally substituted with $C_{1-4}$ alkoxy, 3: a five- to ten-membered heteroaryl-$C_{1-4}$ alkyl group, in which the heteroaryl moiety thereof is optionally substituted with the same or different 1 to 3 groups selected from the group consisting of:
  (a) halogen, and
  (b) $C_{1-4}$ alkyl, or 4: a $C_{6-10}$ aryl $C_{2-6}$ alkenyl group;

Y is a group: —COOR$^9$ or a group: —CONHNH$_2$; and $R^9$ is a hydrogen atom or a $C_{1-6}$ alkyl group.

Advantageous Effects of Invention

The compound represented by Formula (I) or a pharmaceutically acceptable salt thereof (which may be referred to as "the compound of the present invention") exhibits potent glucagon receptor antagonistic activity and can be used in the prevention and/or treatment of symptoms and diseases in which glucagon is involved, such as hyperglycemia, abnormal glucose tolerance, insulin resistance syndrome, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, metabolic syndrome, diabetic complications (cataracts, retinopathy, keratopathy, neuropathy, nephropathy, peripheral circulatory failure, cerebrovascular disorder, ischemic heart disease, arteriosclerosis, etc.), and other such symptoms and diseases.

\*\*: P<0.01, \*\*\*: P<0.001: Significance tests using Tukey's multiple comparison test among the groups of ob/ob mice showed significant differences.

n.s.: There was no significant difference (P>0.05).

Figure 3:
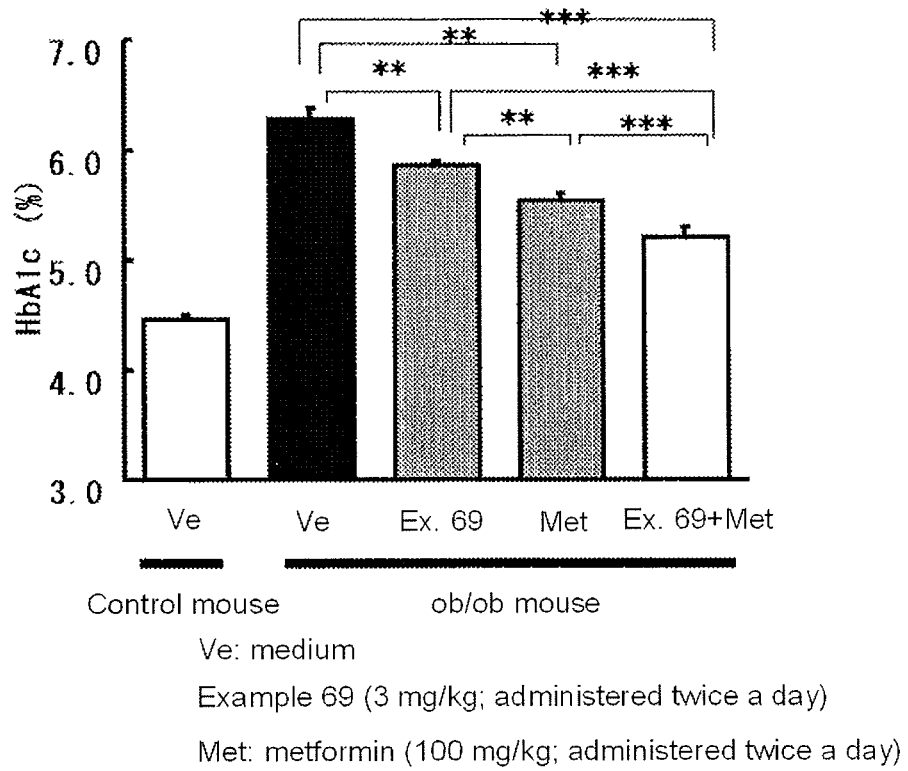

FIG. 3 shows the influence of a four-week administration of the compound of Example 69 in combination with metformin on HbA1c of ob/ob mice. The data is presented as average values±standard error.

\*\*:P<0.01, \*\*\*: P<0.001: Significance tests using Tukey's multiple comparison test among the groups of ob/ob mice showed significant differences.

Figure 4:
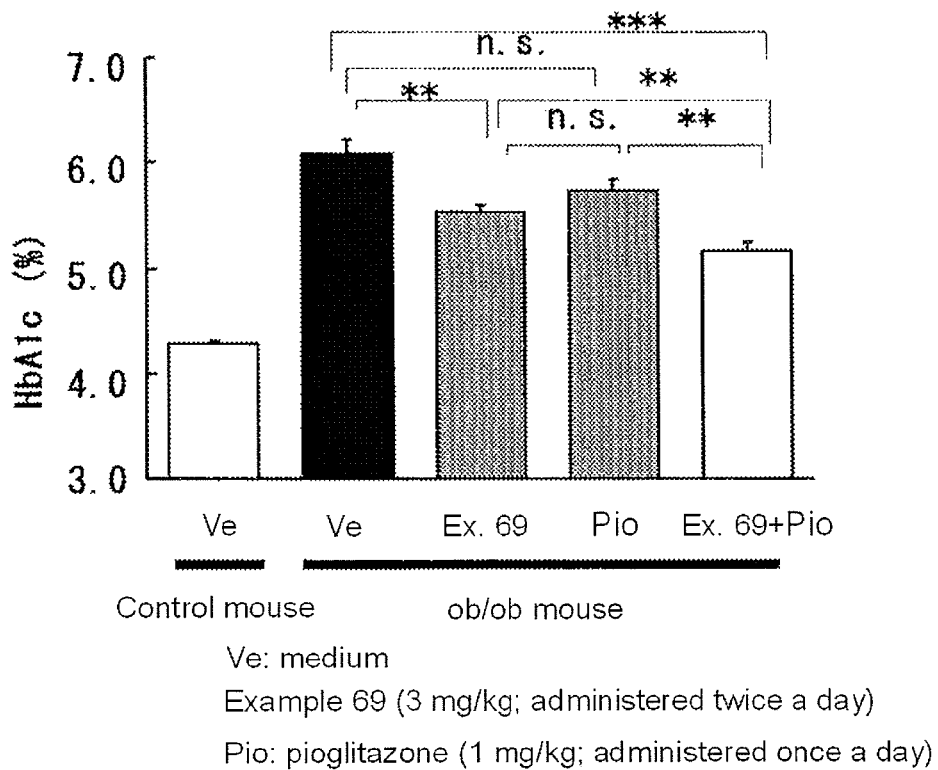

FIG. 4 shows the influence of a four-week administration of the compound of Example 69 in combination with pioglitazone on HbA1c of ob/ob mice.

\*\*:P<0.01, \*\*\*: P<0.001: Significance tests using Tukey's multiple comparison test among the groups of ob/ob mice showed significant differences.

n.s.: There was no significant difference (P>0.05).

DESCRIPTION OF EMBODIMENTS

The present invention is described in more detail below. In the specification, the number of carbon atoms in the definition of a "substituent" is expressed, for example, as "$C_{1-6}$." More specifically, the expression "$C_{1-6}$ alkyl" is synonymous with an alkyl group having 1 to 6 carbon atoms.

The term "group" as used in the specification refers to a monovalent group. For example, the term "alkyl group" refers to a monovalent saturated hydrocarbon group. Moreover, the term "group" is sometimes omitted in the explanation of substituents in the specification.

The number of substituents in groups defined by the phrase "optionally substituted" or "substituted" is not particularly limited as long as the substituents are replaceable, and the number is one or more than one. Moreover, unless otherwise particularly specified, the explanation of each group is also applicable when the groups are part or substituents of other groups. Furthermore, in the specification, groups that are not modified by the phrase "optionally substituted" or "substituted" refer to "unsubstituted" groups. For example, the term "$C_{1-6}$ alkyl" refers to "unsubstituted $C_{1-6}$ alkyl."

Examples of the "halogen atom" include fluorine, chlorine, bromine, iodine, etc.

The term "$C_{1-6}$ alkyl group" refers to a linear or branched saturated hydrocarbon group having 1 to 6 carbon atoms. Preferable is a "$C_{1-4}$ alkyl group." Specific examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, etc. Specific examples of the "$C_{1-4}$ alkyl group" include methyl, ethyl, propyl, isopropyl, butyl, isobutyl, sec-butyl, tert-butyl, etc.

The term "$C_{3-8}$ cycloalkyl group" refers to a cyclic saturated hydrocarbon group having 3 to 8 carbon atoms. Preferable is a "$C_{3-6}$ cycloalkyl group," and more preferable is a "$C_{5-6}$ cycloalkyl group." Specific examples of the "$C_{3-8}$ cycloalkyl group" include cyclopropyl, cyclobutyl, cyclopentyl, cyclohexyl, cycloheptyl, cyclooctyl, etc. Specific examples of the "$C_{3-6}$ cycloalkyl group" include cyclopropyl, cyclobutyl, cyclopentyl, cyclohexyl, etc.

The term "$C_{3-8}$ cycloalkyl $C_{1-4}$ alkyl group" refers to the above "$C_{1-4}$ alkyl group" substituted with the above "$C_{3-8}$ cycloalkyl group." Preferable is a "$C_{3-6}$ cycloalkyl $C_{1-4}$ alkyl group." Specific examples of the "$C_{3-8}$ cycloalkyl $C_{1-4}$ alkyl group" include cyclopropylmethyl, cyclobutylmethyl, cyclopentylmethyl, cyclohexylmethyl, cycloheptylmethyl, cyclooctylmethyl, etc.

The term "$C_{2-6}$ alkenyl group" refers to a linear or branched unsaturated hydrocarbon group having 2 to 6 carbon atoms and including one double bond. Preferable is a "$C_{2-4}$ alkenyl group." Specific examples thereof include vinyl, propenyl, methylpropenyl, butenyl, methylbutenyl, etc.

The term "$C_{6-10}$ aryl group" refers to an aromatic hydrocarbon group having 6 to 10 carbon atoms. Specific examples of the "$C_{6-10}$ aryl group" include phenyl, 1-naphthyl, 2-naphthyl, etc. Preferable is phenyl. This group also includes groups formed by fusion of phenyl rings with $C_{5-6}$ cycloalkyl rings, and the $C_{5-6}$ cycloalkyl moiety thereof may include 1 to 2 hetero atoms selected from nitrogen, sulfur, and oxygen. However, in the case of a polycyclic aryl group formed by fusion of a phenyl ring with a $C_{5-6}$ cycloalkyl ring, the bond of the "group" is attached only to the phenyl ring. Specific examples thereof include groups represented by the following formulae:

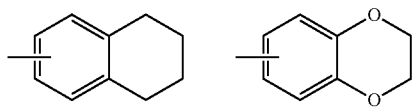

A bond drawn across a ring as shown in the above formulae indicates that the point of attachment of the "group" is any substitutable position of that ring.

The term "$C_{7-14}$ aralkyl group" refers to a "$C_{6-10}$ aryl $C_{1-4}$ alkyl group," indicating the above "$C_{1-4}$ alkyl group" substituted with the above "$C_{6-10}$ aryl group." Preferable is a "$C_{7-10}$ aralkyl group" (phenyl $C_{1-4}$ alkyl group). Specific examples of the "$C_{7-14}$ aralkyl group" include benzyl, 2-phenylethyl, 1-phenylpropyl, 1-naphthylmethyl, etc.

The term "$C_{6-10}$ aryl $C_{2-6}$ alkenyl group" refers to the above "$C_{2-6}$ alkenyl group" substituted with the above "$C_{6-10}$ aryl group." Preferable is a "$C_{6-10}$ aryl $C_{2-4}$ alkenyl group." Specific examples thereof include styryl, cinnamyl, etc.

The "$C_{6-10}$ aryl" of the "$C_{6-10}$ arylcarbonyl group" is as described above. Specific examples thereof include phenylcarbonyl, benzylcarbonyl, etc.

The term "$C_{6-10}$ arylcarbonyl $C_{1-4}$ alkyl group" refers to the above "$C_{1-4}$ alkyl" substituted with the above "$C_{6-10}$ arylcarbonyl." Specific examples thereof include phenacyl, etc.

Examples of the "heteroaryl group" include five- to ten-membered monocyclic or polycyclic aromatic groups. These groups include the same or different one or more (e.g., 1 to 4) heteroatoms selected from nitrogen, sulfur, and oxygen. The "polycyclic heteroaryl group" is preferably a bicyclic or tricyclic group, and more preferably a bicyclic group. The polycyclic heteroaryl group includes those formed by fusion of the above monocyclic heteroaryl groups with aromatic rings (e.g., benzene and pyridine) or with non-aromatic rings (e.g., cyclohexyl). Specific examples of the "heteroaryl group" include groups represented by the following formulae:

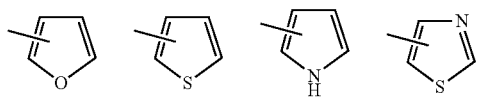

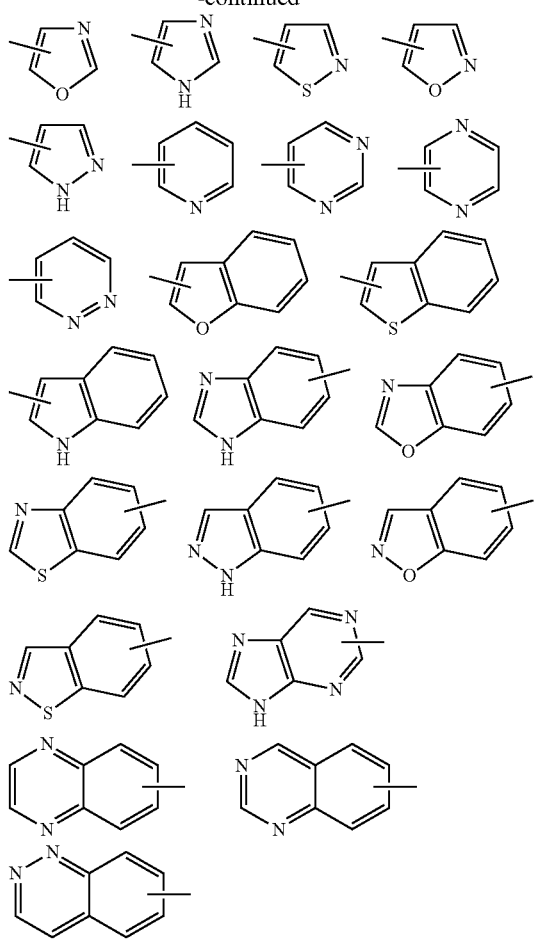

A bond drawn across a ring as shown in the above formulae indicates that the point of attachment of the "group" is any substitutable position of that ring. For example, a heteroaryl group represented by the following formula:

refers to a 2-furyl group or a 3-furyl group.

Moreover, when the "heteroaryl group" is a polycyclic group, for example, one represented by the following formula:

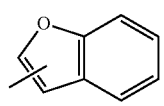

may be 2-benzofuryl, 3-benzofuryl, or 4-, 5-, 6-, or 7-benzofuryl. However, in the case of a polycyclic heteroaryl group formed by fusion of an aromatic ring with a non-aromatic ring (e.g., piperidine), the bond of the "group" is attached only to the aromatic ring. For example, a "polycyclic heteroaryl group" represented by the following formula:

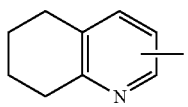

indicates that the "group" is bonded at the 2-, 3-, or 4-position.

The term "heteroaryl $C_{1-4}$ alkyl group" refers to the "$C_{1-4}$ alkyl group" substituted with the above "heteroaryl group." Examples of the heteroaryl moiety include the specific examples of the above-mentioned heteroaryl group. Specific examples of the "heteroaryl $C_{1-4}$ alkyl group" include 2-pyridylmethyl, etc.

The "$C_{1-6}$ alkyl" moiety of the "$C_{1-6}$ alkoxy group" is the same as the "$C_{1-6}$ alkyl" described above. Preferable are a "$C_{1-4}$ alkoxy group," etc. Specific examples of the "$C_{1-6}$ alkoxy group" include methoxy, ethoxy, propoxy, isopropoxy, butoxy, isobutoxy, sec-butoxy, tert-butoxy, pentyloxy, hexyloxy, etc. Specific examples of the "$C_{1-4}$ alkoxy group" include methoxy, ethoxy, propoxy, isopropoxy, butoxy, isobutoxy, sec-butoxy, tert-butoxy, etc.

The term "$C_{1-4}$ alkoxy $C_{1-4}$ alkyl group" refers to a $C_{1-4}$ alkyl group to which the above "$C_{1-4}$ alkoxy group" is bonded. Specific examples thereof include methoxymethyl, ethoxymethyl, etc.

The term "$C_{1-4}$ alkoxycarbonyl group" refers to a carbonyl group to which the above "$C_{1-4}$ alkyl group" is bonded. Specific examples thereof include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, etc.

The term "$C_{1-4}$ alkylcarbonyl group" refers to a carbonyl group to which the above "$C_{1-4}$ alkyl group" is bonded. Specific examples thereof include methylcarbonyl, ethylcarbonyl, propylcarbonyl, isopropylcarbonyl, butylcarbonyl, isobutylcarbonyl, sec-butylcarbonyl, tert-butylcarbonyl, etc.

Examples of the "pharmaceutically acceptable salt" include inorganic acid salts, such as hydrochloride, hydrobromide, sulfate, phosphate, and nitrate; organic acid salts, such as acetate, propionate, oxalate, succinate, lactate, malate, tartrate, citrate, maleate, fumarate, methanesulfonate, benzenesulfonate, p-toluenesulfonate, and ascorbate; inorganic base salts, such as sodium salt, potassium salt, calcium salt, zinc salt, magnesium salt, and aluminum salt; and organic base salts, such as arginine salt, benzathine salt, choline salt, diethylamine salt, diol amine salt, glycine salt, lysine salt, meglumine salt, olamine salt, and tromethamine salt.

The present invention includes a compound represented by Formula (I) or a pharmaceutically acceptable salt or prodrug thereof. The present invention also includes hydrates thereof or solvates (e.g., ethanol solvate). Additionally, the present invention includes various crystal forms.

The phrase "the prodrug of the compound of Formula (I)" as used in the specification refers to a compound convertible to the compound of Formula (I) by reaction with enzyme, gastric acid, etc., under in vivo physiological conditions; for example, a compound convertible to the compound of Formula (I) by enzymatic oxidation, reduction, hydrolysis, etc.; and a compound convertible to the compound of Formula (I) by hydrolysis with gastric acid, etc.

The compound of Formula (I) may exist as a tautomer. Accordingly, the present invention includes tautomers of the compound of Formula (I) as well.

The compound of the present invention may have at least one asymmetric carbon atom. Accordingly, the present invention includes not only racemates but also optically active substances of the compound of the present invention. When the compound of the present invention has two or more asymmetric carbon atoms, stereoisomerism may occur. Accordingly, the present invention includes stereoisomers of the compound of the present invention and mixtures thereof as well.

Preferable examples of the compound of the present invention are described. In the compound of the present invention, $R^1$ is preferably a $C_{7-14}$ aralkyl group, in which the aryl moiety thereof is substituted with the same or different 1 to 3 groups selected from the group consisting of:
(a) a halogen atom;
(b) a $C_{1-4}$ alkyl group, which is optionally substituted with 1 to 3 fluorine atoms;
(c) a $C_{1-4}$ alkoxy group, which is optionally substituted with 1 to 3 fluorine atoms; and
(d) a $C_{1-4}$ alkylcarbonyl group, which is optionally substituted with $C_{1-4}$ alkoxy.

The substituent of the $C_{7-14}$ aralkyl group in $R^1$ is preferably a $C_{1-4}$ alkyl group optionally substituted with 1 to 3 fluorine atoms, and more preferably a methyl group, an ethyl group, a 2-propyl group, or a 1,1,1-trimethylmethyl group.

$R^1$ is preferably a 1-phenylethyl group, in which the phenyl moiety thereof is substituted with the same or different 1 to 3 groups selected from the group consisting of:
(a) a halogen atom;
(b) a $C_{1-4}$ alkyl group, which is optionally substituted with 1 to 3 fluorine atoms;
(c) a $C_{1-4}$ alkoxy group, which is optionally substituted with 1 to 3 fluorine atoms; and
(d) a $C_{1-4}$ alkylcarbonyl group, which is optionally substituted with $C_{1-4}$ alkoxy.

More preferable is a 1-phenylethyl group, in which the phenyl moiety thereof is substituted with a halogen atom or a $C_{1-4}$ alkyl group optionally substituted with 1 to 3 fluorine atoms, and still more preferable is a 1-phenylethyl group in which the phenyl group thereof is substituted with a methyl group, an ethyl group, a 2-propyl group, a 1,1,1-trimethylmethyl group, a fluorine atom, a chlorine atom, or a bromine atom.

The 1-phenylethyl group in $R^1$ is still more preferably a (1S)-1-phenylethyl group, which is an enantiomer.

$R^1$ is preferably a 1-(4-methylphenyl)ethyl group, a 1-(4-fluorophenyl)ethyl group, a 1-phenylethyl group, 1-(4-chlorophenyl)ethyl group, a 1-(4-(3,4-dimethylphenyl)phenyl)ethyl group, a 1-(4-chloro-3-methylphenyl)ethyl group, a 1-(4-chloro-2-fluorophenyl)ethyl group, or a 1-(4-ethylphenyl)ethyl group; more preferably a 1-(4-ethylphenyl)ethyl group, a 1-(4-methylphenyl)ethyl group, or a 1-(4-fluorophenyl)ethyl group; and particularly preferably a 1-(4-ethylphenyl)ethyl group, a (1S)-1-(4-methylphenyl)ethyl group, or a (1S)-1-(4-fluorophenyl)ethyl group.

$R^2$ is preferably a nitro group.

Other preferred embodiments of the present invention are described.

(1) A compound represented by Formula (II) or a pharmaceutically acceptable salt thereof:

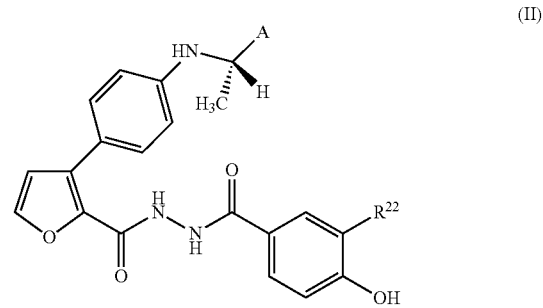

(II)

wherein A and $R^{22}$ are as defined above.

In the compound represented by Formula (II), A is preferably a compound represented by the following formula:

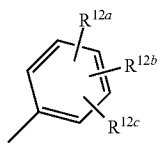

(a)

wherein $R^{12a}$, $R^{12b}$, and $R^{12c}$ are as defined above; and $R^{22}$ is preferably a nitro group.

(2) A compound represented by Formula (III) or a pharmaceutically acceptable salt thereof:

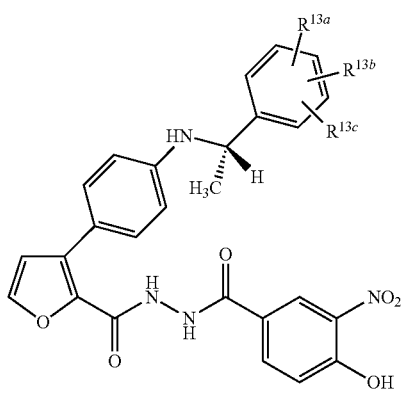

(III)

wherein $R^{13a}$, $R^{13b}$, and $R^{13c}$ are as defined above.

The present invention also includes production intermediates of the compound represented by Formula (I). Examples of the production intermediate include a compound represented by the following formula:

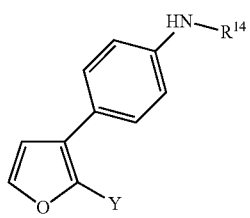

(IV)

wherein the symbols are as defined above.

The method for producing the compound represented by Formula (I) of the present invention is described below with reference to examples; however, the present invention is not limited thereto.

The compound represented by Formula (I) can be synthesized from a known compound by a combination of known methods. For example, the compound can be synthesized in the following manner. The compound represented by Formula (I) can be produced by the methods described below, depending on the type of starting material.

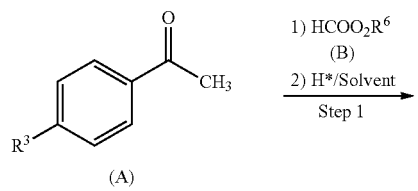

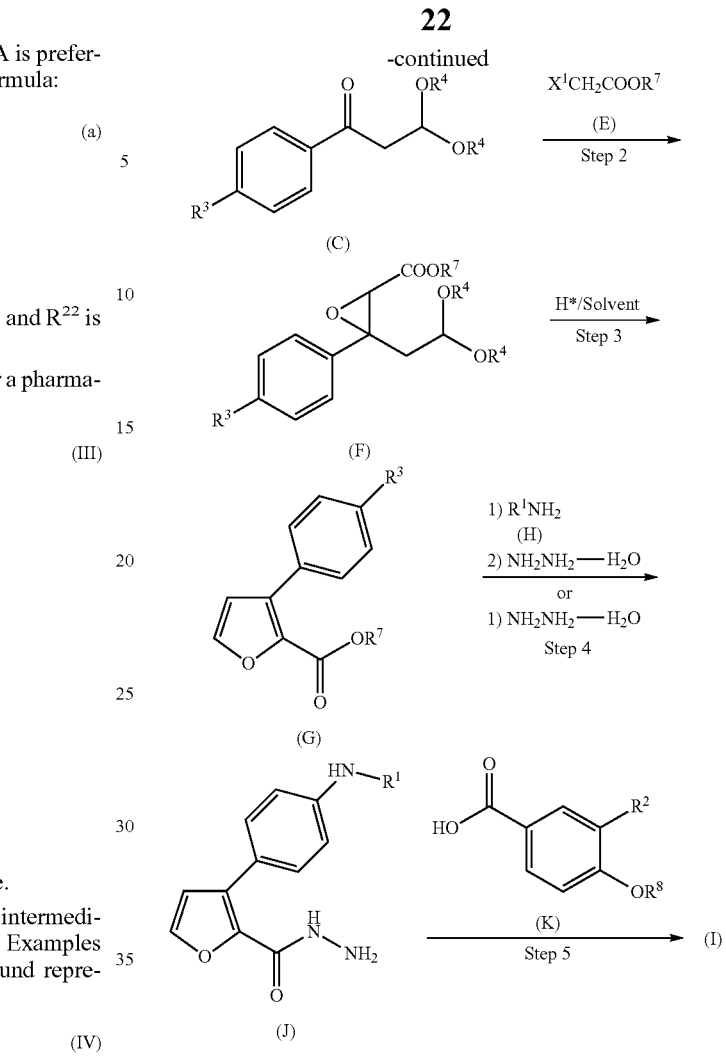

wherein the symbols are as defined above.

Step 1

Compound (A) is reacted with Compound (B) in the presence of a base, and the obtained compound is reacted in the presence of an acid, thereby obtaining Compound (C) (Step 1).

The amount of Compound (B) used is 0.8 to 4 equivalents, preferably 1 to 2 equivalents, and more preferably 1.2 to 1.7 equivalents, relative to Compound (A).

The base used in Step 1 is preferably an alkali metal alkoxide (e.g. sodium methoxide, sodium ethoxide, or potassium tert-butoxide), and particularly preferably sodium methoxide.

This reaction is advantageously performed in a solvent. Although the solvent is not specified as long as it does not affect the reaction, an aprotic solvent is preferred. Examples of aprotic solvents include nitrile solvents (e.g., acetonitrile), ether solvents (e.g., tetrahydrofuran, diethyl ether, diisopropyl ether, dioxane, and dimethoxyethane), amide solvents (e.g., N,N-dimethylformamide, N,N-dimethylacetamide, and N-methylpyrrolidone), halogenated-hydrocarbon solvents (e.g., dichloromethane, chloroform, carbon tetrachloride, 1,2-dichloroethane, and chlorobenzene), hydrocarbon solvents (e.g., hexane, benzene, and toluene), and the like. These may be used as a mixed solvent. Preferred aprotic solvents are ether solvents (e.g., diethyl ether, dioxane, and tetrahydrofuran).

The amount of base used is 1 to 3 equivalents, preferably 1 to 2 equivalents, and particularly preferably 1.2 to 1.7 equivalents, relative to Compound (A).

The reaction temperature of the reaction in the presence of a base is −50 to 100° C., and preferably 0 to 80° C. The reaction time is 0.5 to 36 hours, and preferably 1 to 5 hours.

This reaction is followed by a reaction in the presence of an acid to thereby obtain Compound (C). The acid used in the reaction may be either an organic or inorganic acid. Examples of organic acids include trifluoroacetic acid, methanesulfonic acid, paratoluenesulfonic acid, benzenesulfonic acid, etc. Examples of inorganic acids include hydrochloric acid, sulfuric acid, nitric acid, phosphoric acid, boric acid, hydrogen bromide, hydrofluoric acid, hydrogen iodide, etc.

The acid used in the reaction is preferably methanesulfonic acid, paratoluenesulfonic acid, benzenesulfonic acid, hydrochloric acid, sulfuric acid, hydrogen bromide, nitric acid, etc., and particularly preferably sulfuric acid.

The amount of acid used in the reaction is 1 to 10 equivalents, preferably 1 to 3 equivalents, and particularly preferably 1.2 to 2 equivalents, relative to Compound (A).

This reaction is advantageously performed in a solvent that generally does not affect the reaction. The solvent is preferably an alcoholic solvent (e.g., methanol, ethanol, 2-propanol, or tert-butanol), and particularly preferably methanol or ethanol.

The reaction temperature is -30 to 100° C., and preferably 0 to 80° C. The reaction time is 1 to 48 hours, and preferably 4 to 24 hours. This reaction can be advantageously carried out simply by a continuous one-pot process without purification.

Moreover, when $R^3$ is a group: —$N(R^1)(R^5)$, $R^5$ may be a $C_{1-4}$ alkoxycarbonyl group or a $C_{7-14}$ aralkyl group. In this case, deprotection may be performed in any of steps 2 to 4, described later, and $R^3$ may be used as a compound of the group: —$NH(R^1)$ to perform a reaction of any of steps 2 to 4. Deprotection can be performed by, for example, a reduction reaction by hydrogenation using a metal catalyst (e.g., palladium).

Step 2

Compound (C) is reacted with Compound (E), thereby obtaining Compound (F).

As Compound (E), a commercially available compound can be used; alternatively, Compound (E) can be obtained by esterifying a compound represented by the following formula:

$$X^1CH_2COOH \quad (D)$$

wherein $X^1$ is as defined above, using a known reagents (e.g., N,N'-dicyclohexylcarbodiimide or 4-dimethylaminopyridine).

The amount of Compound (E) used is 0.8 to 5 equivalents, preferably 1 to 3 equivalents, and more preferably 1.2 to 2 equivalents, relative to Compound (C). Examples of Compound (E) include methyl α-chloroacetate, ethyl α-chloroacetate, propyl α-chloroacetate, isopropyl α-chloroacetate, n-butyl α-chloroacetate, isobutyl α-chloroacetate, tert-butyl α-chloroacetate, cyclohexyl a-chloroacetate, phenyl α-chloroacetate, benzyl α-chloroacetate, methyl α-bromoacetate, ethyl α-bromoacetate, propyl α-bromoacetate, isopropyl α-bromoacetate, tert-butyl α-bromoacetate, phenyl α-bromoacetate, benzyl α-bromoacetate, ethyl α-iodoacetate, 4-nitrobenzyl α-bromoacetate, etc. Compound (E) is preferably methyl α-chloroacetate, ethyl α-chloroacetate, methyl α-bromoacetate, or ethyl α-bromoacetate.

This reaction is advantageously performed in a solvent that generally does not affect the reaction. The solvent is preferably an aprotic solvent. Examples of aprotic solvents include nitrile solvents (e.g., acetonitrile), ether solvents (e.g., tetrahydrofuran, diethyl ether, diisopropyl ether, dioxane, and dimethoxyethane), amide solvents (e.g., N,N-dimethylformamide, N,N-dimethylacetamide, and N-methylpyrrolidone), halogenated-hydrocarbon solvents (e.g., dichloromethane, chloroform, carbon tetrachloride, 1,2-dichloroethane, and chlorobenzene), ester solvents (e.g., ethyl formate, ethyl acetate, and tert-butyl acetate), ketone solvents (e.g., acetone, methyl ethyl ketone, and methyl isobutyl ketone), hydrocarbon solvents (e.g., hexane, benzene, and toluene), and the like. These may be used as a mixed solvent. Preferred aprotic solvents are ether solvents (e.g., diethyl ether, dioxane, and tetrahydrofuran). The reaction temperature is −50 to 100° C., and preferably −30 to 60° C. The reaction time is 1 to 24 hours, and preferably 1 to 8 hours.

Examples of the base used in this reaction include the same bases used in Step 1. Particularly preferable are alkali metal alkoxides (e.g., sodium methoxide, sodium ethoxide, and potassium tert-butoxide). The base used is an alkali metal alkoxide of an alcohol ($R^7OH$) corresponding to the $R^7O$ group of Compound (E).

Step 3

Compound (F) is reacted in the presence of an acid to thereby obtain Compound (G). The acid used in the reaction is organic acids (e.g., trifluoroacetic acid, methanesulfonic acid, paratoluenesulfonic acid, benzenesulfonic acid, benzoic acid, oxalic acid, fumaric acid, maleic acid, citric acid, and acetic acid) or inorganic acids (e.g., hydrochloric acid, sulfuric acid, nitric acid, phosphoric acid, boric acid, hydrogen bromide, hydrofluoric acid, and hydrogen iodide).

The amount of acid used in the reaction is 0.01 to 3 equivalents, preferably 0.05 to 1 equivalent, and particularly preferably 0.1 to 0.5 equivalents, relative to Compound (F).

This reaction is advantageously performed in a solvent that generally does not affect the reaction. Examples of the solvent include nitrile solvents (e.g., acetonitrile), ether solvents (e.g., tetrahydrofuran, diethyl ether, diisopropyl ether, dioxane, and dimethoxyethane), amide solvents (e.g., N,N-dimethylformamide, N,N-dimethylacetamide, and N-methylpyrrolidone), halogenated-hydrocarbon solvents (e.g., dichloromethane, chloroform, carbon tetrachloride, 1,2-dichloroethane, and chlorobenzene), ester solvents (e.g., ethyl formate, ethyl acetate, and tert-butyl acetate), ketone solvents (e.g., acetone, methyl ethyl ketone, and methyl isobutyl ketone), and hydrocarbon solvents (e.g., hexane, benzene, and toluene). Preferable are hydrocarbon solvents (e.g., hexane, benzene, and toluene).

The reaction temperature is 0 to 150° C., and preferably 40 to 100° C. The reaction time is 0.5 to 24 hours, and preferably 1 to 5 hours. This reaction can be advantageously carried out simply by a continuous one-pot process without purification.

Step 4

Compound (G) is reacted with Compound (H) and then reacted with hydrazine monohydrate, or Compound (G) is reacted with hydrazine monohydrate, thereby obtaining Compound (J).

1) When $R^3$ is a Halogen Atom:

Compound (G) is reacted with Compound (H) in the presence of a base and a metal catalyst (transition metal). The amount of Compound (H) used is 0.8 to 3 equivalents, preferably 0.8 to 2 equivalents, and more preferably 1 to 1.5 equivalents, relative to Compound (G). Examples of the compound (H) include benzylamine, phenethylamine, 1-phenylethylamine, 1-methyl-3-phenylpropylamine, 1-(1-naphthyl)ethylamine, 1-(2-naphthyl)ethylamine, 1-thiophen-2-yl-ethylamine, 1-thiophen-3-yl-ethylamine, 1-furan-2-yl-ethylamine, 1-furan-3-yl-ethylamine, 1-benzofuran-2-ylethylamine, 1-benzofuran-3-yl-ethylamine, 1-benzo[B]thiophen-2-yl-ethylamine, 1-benzo[B]thiophen-3-yl-ethylamine, 4-phenylbut-3-en-2-ylamine, etc.

The base used in the reaction in case 1) above is preferably an alkali metal alkoxide (e.g., sodium methoxide, sodium ethoxide, or potassium tert-butoxide) or an alkaline carbonate metal salt (e.g., sodium carbonate, potassium carbonate, or cesium carbonate), and particularly preferably potassium tert-butoxide.

The amount of base used in the reaction is 0.8 to 3 equivalents, preferably 1 to 2 equivalents, and particularly preferably 1 to 1.5 equivalents, relative to Compound (G).

This reaction is advantageously performed in a solvent. The solvent is not specified as long as it does not affect the reaction. Examples thereof include alcohol solvents (e.g., methanol, ethanol, propanol, 2-propanol, and tert-butanol), nitrile solvents (e.g., acetonitrile), ether solvents (e.g., tetrahydrofuran, diethyl ether, diisopropyl ether, dioxane, and dimethoxyethane), amide solvents (e.g., N,N-dimethylformamide, N,N-dimethylacetamide, and N-methylpyrrolidone), halogenated-hydrocarbon solvents (e.g., dichloromethane, chloroform, carbon tetrachloride, 1,2-dichloroethane, and chlorobenzene), hydrocarbon solvents (e.g., hexane, benzene, and toluene), and the like. Preferable are hydrocarbon solvents (e.g., hexane, benzene, and toluene).

The transition metal as a metal catalyst used in the reaction is preferably palladium, nickel, copper, or the like, and particularly preferably palladium. Examples of metal catalysts comprising palladium (palladium catalysts) include divalent palladium compounds typified by palladium acetate, palladium chloride, palladium bromide, palladium acetylacetonate, palladium propionate, Dichloro (1,5-cyclooctadiene) palladium, bis(triphenylphosphine)palladium dichloride, palladium nitrate, and bis(benzonitrile)palladium chloride; and zero-valent palladium compounds typified by bis(tri-O-tolylphosphine)palladium, bis(dibenzylideneacetone)palladium, tris(dibenzylideneacetone)dipalladium, tetrakis(triphenylphosphine)palladium, and palladium carbon. Particularly preferable is palladium acetate.

The amount of palladium catalyst used in the reaction is 0.001 to 1 equivalent, preferably 0.001 to 0.1 equivalent, and particularly preferably 0.005 to 0.05 equivalents, relative to Compound (G).

When a metal catalyst is used, ligands may be used. Examples of ligands usable in the reaction include 2,2'-bis(diphenylphosphino)-1,1'-binaphthyl, 1-[2-[bis(tert-butyl)phosphino]phenyl]-3,5-diphenyl-1H-pyrazole, 5-(di-tert-butylphosphino)-1',3',5'-triphenyl-1'H-[1,4']bipyrazole, 2-dicyclohexylphosphino-2',4',6'-triisopropyldiphenyl, 2-di-tert-butylphosphino-2',4',6'-triisopropyldiphenyl, 2-dicyclohexylphosphino-2',6'-diisopropyldiphenyl, 2-dicyclohexylphosphino-2',6'-dimethoxydiphenyl, 2-dicyclohexylphosphino-2'-(N,N-dimethylamino)diphenyl, etc. Preferable is 2,2'-bis(diphenylphosphino)-1,1'-binaphthyl.

The amount of ligand used in the reaction is 0.001 to 1 equivalent, preferably 0.001 to 0.1 equivalent, and particularly preferably 0.005 to 0.05 equivalents, relative to Compound (G).

The reaction temperature is 25 to 150° C., and preferably 50 to 100° C. The reaction time is 0.5 to 24 hours, and preferably 1 to 5 hours. This reaction can be advantageously carried out simply by a continuous one-pot process without purification.

The compound obtained by the reaction of Compound (G) with Compound (H) is reacted with hydrazine monohydrate to thereby obtain Compound (J). The amount of hydrazine monohydrate used in the reaction is 1 to 30 equivalents, preferably 1 to 10 equivalents, and more preferably 1 to 3 equivalents, relative to Compound (G).

This reaction is advantageously performed in a solvent that generally does not affect the reaction. Examples of the solvent include alcohol solvents (e.g., methanol, ethanol, 2-propanol, and tert-butanol), ether solvents (e.g., tetrahydrofuran, diethyl ether, diisopropyl ether, dioxane, and dimethoxyethane), and the like. Particularly preferable are methanol, ethanol, tetrahydrofuran, and dioxane.

The reaction temperature is 0 to 150° C., and preferably 30 to 100° C. The reaction time is 1 to 36 hours, and preferably 1 to 4 hours.

2) When $R^3$ is other than a Halogen Atom:

Compound (G) is reacted with hydrazine monohydrate, thereby obtaining Compound (J). The reaction conditions of hydrazination are the same as those described above.

Step 5

Compound (J) is reacted with Compound (K), thereby obtaining the compound represented by Formula (I). The amount of Compound (K) used in the reaction is 0.8 to 3 equivalents, preferably 0.8 to 1.5 equivalents, and particularly preferably 1 to 1.3 equivalents, relative to Compound (J).

In this reaction, commercially available Compound (K) and commercially available Compound M (e.g., thionyl chloride, oxalyl chloride, phosphorus trichloride, phosphorus pentachloride, N,N'-carbonyldiimidazole, trichloroacetyl chloride, diphenylphosphoryl azide, diphenylphosphinyl chloride, ethyl chlorocarbonate, isobutyl chlorocarbonate, and pivaloyl chloride) may be converted to acid halides, mixed acid anhydrides, or highly reactive compounds (e.g., acylimidazole and acyl azide) by a known method, followed by a reaction with Compound (J). Moreover, Compound (K) and Compound M as described above may be reacted at the same time. Furthermore, a suitable combination of commercially available Compound N (dicyclohexylcarbodiimide, diisopropylcarbodiimide, N-ethyl-N'-3-dimethylaminopropyl carbodiimide or hydrochloride thereof, benzotriazol-1-yl-tris(dimethylamino)phosphonium hexafluorophosphate, or (benzotriazol-1-yloxy)tripyrrolidinophosphonium hexafluorophosphate) with commercially available Compound O (1-hydroxybenzotriazole or N-hydroxysuccinimide), or Compound N alone may be reacted with Compounds (J) and (K) simultaneously.

Although the solvent is not specified as long as it does not affect the reaction, an aprotic solvent is preferable. Examples of aprotic solvents include nitrile solvents (e.g., acetonitrile), ether solvents (e.g., tetrahydrofuran, diethyl ether, diisopropyl ether, dioxane, and dimethoxyethane), amide solvents (e.g., N,N-dimethylformamide, N,N-dimethylacetamide, and N-methylpyrrolidone), halogenated-hydrocarbon solvents (e.g., dichloromethane, chloroform, carbon tetrachloride, 1,2-dichloroethane, and chlorobenzene), ester solvents (e.g., ethyl formate, ethyl acetate, and tert-butyl acetate), ketone solvents (e.g., acetone, methyl ethyl ketone, and methyl isobutyl ketone), and hydrocarbon solvents (e.g., hexane, benzene, and toluene). Preferable among these are ether solvents, halogenated-hydrocarbon solvents, ester solvents, and amide solvents. Particularly preferable are tetrahydrofuran, dioxane, ethyl acetate, N,N-dimethylformamide, N,N-dimethylacetamide, and N-methylpyrrolidone.

The reaction temperature is -20 to 100° C., and preferably 0 to 80° C. The reaction time is 0.5 to 36 hours, and preferably 1 to 3 hours.

When Compound (K) is a compound wherein $R^8$ is other than a hydrogen atom, Compound (K) is reacted with Compound (J), followed by deprotection using a known method, thereby obtaining the compound represented by Formula (I).

None of steps 1 to 5 uses column chromatography, and the compound represented by Formula (I) is isolated and purified in step 5, thereby obtaining the compound represented by Formula (I).

A compound represented by Formula (G) wherein $R^7$ is a hydrogen atom (Compound (G')) can also produce a compound represented by Formula (J) according to the formula shown below.

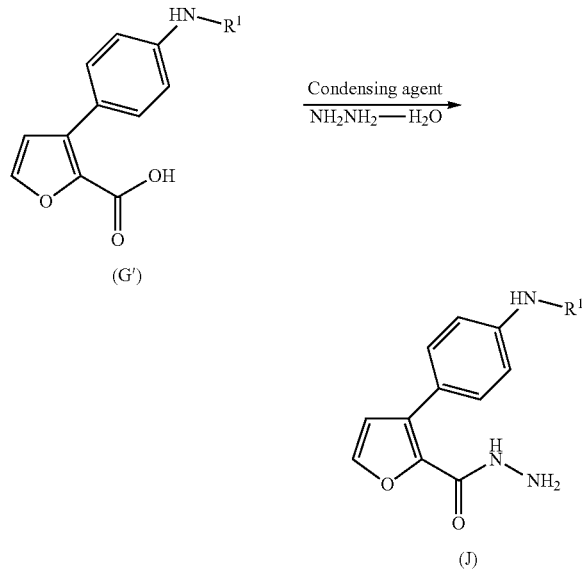

wherein $R^1$ is as defined above.

The compound represented by Formula (G') is reacted with a condensing agent, followed by hydrazidation. Examples of condensing agents include the commercial products described above as the examples of Compound N. Hydrazidation can be carried out under the same conditions as in Step 4. The compound represented by Formula (G') can be produced by hydrolyzing a compound represented by Formula (G) (wherein $R^3$ is a group: —NH($R^1$)) under acidic or basic conditions according to a known method.

The thus-obtained compound represented by Formula (J) is subjected to the same reaction as in Step 5 to thereby produce a compound represented by Formula (I). The compound represented by Formula (G) wherein $R^7$ is a hydrogen atom can be produced by using a commercially available reagent and a known method. Accordingly, the compound represented by Formula (I) can be produced from a compound represented by Formula (IV) according to the formula shown below.

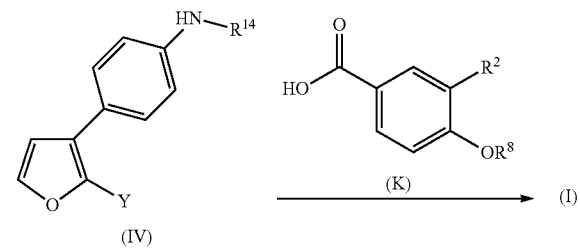

wherein the symbols are as defined above.

The compound represented by Formula (I) may be converted to a pharmaceutically acceptable salt thereof, if necessary, using a known method.

The compound of the present invention includes compounds having an optically active center. Accordingly, the racemates obtained from the compound of the present invention having an optically active center can be physically or chemically divided into their optical antipodes by a known method (e.g., a fractional recrystallization method, chiral column method, or diastereomer method). Alternatively, they can also be obtained by using optically active starting materials.

Owing to the glucagon receptor antagonistic activity, the compound of the present invention is of use as a therapeutic and/or preventive agent for symptoms and diseases in which glucagon is involved, such as hyperglycemia, abnormal glucose tolerance, insulin resistance syndrome, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, metabolic syndrome, diabetic complications (cataract, retinopathy, keratopathy, neuropathy, nephropathy, peripheral circulatory failure, cerebrovascular disorder, ischemic heart disease, arteriosclerosis, etc.), and like symptoms and diseases. In particular, the compound of the present invention is of use as a therapeutic and/or preventive agent for diabetes, particularly for type II diabetes.

These preventive and/or therapeutic agents can be administered orally or parenterally.

When the compound of the present invention is used as a therapeutic agent (drug) as described above, the content of the compound of the present invention is 0.1 to 100 wt. % of the entire drug.

The dose of the compound of the present invention or a drug comprising the compound of the present invention varies depending on the subject of administration, route of administration, diseases, etc.; for example, when the compound or drug is orally administered to an adult of about 60 kg as a therapeutic agent for diabetes, etc., the amount of the compound of the present invention administered is about 0.01 to 1,000 mg, preferably about 0.01 to 500 mg, and more preferably 0.1 to 100 mg. This dose can be administered once or several times a day.

The compound of the present invention and the drug comprising the compound of the present invention may be administered before, between, or after meals, or at bedtime.

Pharmaceutical preparations used in the present invention may comprise pharmaceutically acceptable components other than the compound of the present invention as active ingredients. Examples of such components include excipients, stabilizers, etc. As long as the object of the present invention is achieved, these components are not limited and can be suitably used in suitable proportions. Specific examples of dosage forms include tablets (including sugar-coated tablets and film-coated tablets), pills, capsules (including microcapsules), granules, subtle granules, powders, syrups, emulsions, suspensions, injections, inhalants, ointments, ophthalmic solutions, etc. These pharmaceutical preparations can be prepared by a general method (e.g., a method described in Japanese pharmacopoeia).

More specifically, tablets can be produced by forming the compound of the present invention as it is or a homogeneous mixture thereof with excipients, lubricants, binders, disintegrators, or other suitable additives into granules by a suitable method, followed by compression molding with the addition of lubricants, etc.; or by directly compression-molding the compound of the present invention as it is or a homogeneous mixture thereof with excipients, lubricants, binders, disintegrators, or other suitable additives.

Examples of excipients include lactose, saccharose, D-mannitol, D-sorbitol, starch, pregelatinized starch, dextrin, crystalline cellulose, low-substituted hydroxypropyl cellulose, sodium carboxy methylcellulose, gum arabic, pullulan, light anhydrous silicic acid, synthetic aluminum silicate, magnesium aluminometasilicate, etc.

Examples of lubricants include magnesium stearate, calcium stearate, talc, colloidal silica, etc.

Examples of binders include pregelatinized starch, sucrose, gelatin, gum arabic, methyl cellulose, carboxymethyl cellulose, sodium carboxymethyl cellulose, crystalline cellulose, saccharose, D-mannitol, trehalose, dextrin, pullulan, hydroxypropyl cellulose, hydroxypropyl methylcellulose, polyvinyl pyrrolidone, etc.

Examples of disintegrators include lactose, saccharose, starch, carboxymethyl cellulose, calcium carboxymethyl cellulose, croscarmellose sodium, sodium carboxymethyl starch, light anhydrous silicic acid, low-substituted hydroxypropyl cellulose, etc.

Injections can be produced in such a manner that a certain amount of the compound of the present invention is dissolved, suspended, or emulsified in water for injection, physiological saline, Ringer's solution, or the like to form an aqueous solvent, or generally in vegetable oil to form a nonaqueous solvent; and a certain amount of aqueous solvent or nonaqueous solvent is sealed in a container for injection. Alternatively, injections can be produced by sealing a certain amount of the compound of the present invention in a container for injection.

Examples of carriers for oral preparations include substances generally used in the field of pharmaceutical preparations, such as starch, D-mannitol, crystalline cellulose, and sodium carboxymethyl cellulose. Examples of carriers for injection include distilled water, physiological saline, glucose solution, transfusion, etc. Additionally, additives used in general pharmaceutical preparations can be suitably added.

The compound of the present invention may be used in combination with drugs, such as therapeutic agents for diabetes, therapeutic agents for diabetic complications, antihyperlipidemic agents, antihypertensive agents, anti-obesity agents, and diuretics (hereafter abbreviated as "concomitant drugs") to enhance the effect of the compound. The timing for administration of the compound of the present invention and concomitant drugs is not limited. They may be administered to a patient simultaneously or at time intervals. Moreover, the compound of the present invention and a concomitant drug may be combined to form a combined drug. The dose of the concomitant drug can be suitably determined on the basis of clinically used doses. The proportion of the compound of the present invention and the concomitant drug can be suitably determined, depending on the subject of administration, route of administration, target disease, symptoms, combination, etc. For example, when the subject of administration is human, 0.01 to 5000 parts by weight of the concomitant drug may be used relative to 1 part by weight of the compound of the present invention.

Examples of therapeutic agents for diabetes include insulin preparations (e.g., animal insulin preparations extracted from the pancreas of cattle and pigs, and human insulin preparations synthesized by a genetic engineering method using *E. coli* and yeast), insulin resistance improving agents (e.g., V-411, VVP-808, MSD-9, metaglidasen, PN-2034, isaglitazone, darglitazone, darglitazone, lobeglitazone, MBX-2044, balaglitazone, rivoglitazone, AMG-131, LL-6531, KRP-101, SAR-351034, THR-0921, GSK-376501, aleglitazar, chiglitazar, AVE-0897, indeglitazar, DB-900, DB-959, AGX-0104, DSP-8658, ZYH-2, PRB-2, pioglitazone hydrochloride, troglitazone, rosiglitazone maleate, GI-262570, JTT-501, MCC-555, YM-440, KRP-297, and CS-011), α-glucosidase inhibitors (e.g., voglibose, acarbose, miglitol, and MBI-3253), biguanides (e.g., metformin hydrochloride), insulin secretagogues (e.g., sulfonylurea agents, such as tolbutamide, glibenclamide, gliclazide, chlorpropamide, tolazamide, acetohexamide, glyclopyramide, and glimepiride; fast-acting insulin secretagogues, such as repaglinide, senaglinide, nateglinide, and mitiglinide; and GPR119 agonists), GLP-1 (e.g., GPR120 agonists), GLP-1 analogs (e.g., exenatide, liraglutide, SUN-E7001, AVE010, BIM-51077, and CJC1131), GLP-1 secretagogues (e.g., albiglutide, TTP-054, ZYD-1, MAR-701, LY-2428757, glucagon-like peptide-1, exendin-4, liraglutide, lixisenatide, taspoglutide, PC-DAC:Exendin-4, PF-4856883, PGC-HC-E/GLP-1, GLP-1-Fc, E-XTEN, AC-2592 (GLP-1(7-36)amide), ORMD-0901, NN-9924, and MKC-253), protein tyrosine phosphatase inhibitors (e.g., vanadic acid), β3-agonists (e.g., GW-427353B and N-5984), DPPIV inhibitors (e.g., teneligliptin, TA-6666, linagliptin, dutogliptin, alogliptin, KRP-104, melogliptin, SK-0403, ARI-2243, ALS-2-0426, LC15-0133, SYR-472, TAK-100, DB-160, DA-1229, LC15-0444, DSP-7238, sitagliptin phosphate hydrate, vildagliptin, saxagliptin, and SYR-322), amyrin agonists (e.g., pramlintide), gluconeogenesis inhibitors (e.g., glycogen phosphorylase inhibitors, glucose-6-phosphatase inhibitors, fructose-1,6-bisphosphatase inhibitors, and glucokinase activators), SGLT (sodium-glucose cotransporter) inhibitors (e.g., T-1095), 11β-HSD1 inhibitors (e.g., INCB-13739, AMG-221, JTT-654, and BVT-3498), adiponectin or adiponectin receptor agonists, leptin resistance improving drugs, somatostatin receptor agonists, AMPK activators, islet amyloid polypeptide, anti-CD20 antibody, anti-CD3 antibody, anti-IL-1β antibody, aromatase inhibitors, cannabinoid antagonists, carnitine palmitoyl transferase inhibitors, CD80 expression inhibitors, CD86 expression inhibitors, CD40 expression inhibitors, monocyte chemotactic factor MCP-1 inhibitors, diacylglycerol acyltransferase inhibitors, dopamine inhibitors, farnesoid X receptor agonists, fatty acid synthetase inhibitors, fibroblast activation protein, GPR43-binding substances, glucagon receptor expression inhibitors, GHS receptor inhibitors, glucagon receptor antagonists, histone deacetylase activators, IL-1 receptor antagonists, IL-6 production inhibitors, IKK inhibitors, MTP inhibitors, NF-KappaB inhibitors, lipid peroxidation inhibitors, mTOR inhibitors, nicotinic acid receptor agonists, protein kinase activators, PTP-1B inhibitors, PTPN1 expression inhibitors, semicarbazide-sensitive amine oxidase inhibitors, SLC5A2 expression inhibitors, carbonic anhydrase inhibitors, soluble epoxide hydrolase, STAT-3 inhibitors, TNF production inhibitors, vesicular transporter protein (VMAT1 and VMAT2)-binding substances, zonulin receptor antagonists, human Langerhans islet regeneration-related protein, interleukin-1, interleukin-2, adenosine agonists, tagatose, etc.

Examples of therapeutic agents for diabetic complications include aldose reductase inhibitors (e.g., tolrestat, epalrestat, zenarestat, zopolrestat, minarestat, fidarestat, ranirestat, and CT-112), neurotrophic factors (e.g., NGF, NT-3, and BDNF), PKC inhibitors (e.g., ruboxistaurin mesylate), AGE inhibitors (e.g., ALT946, pimagedine, piratoxathin, and N-phenacylthiazolium bromide (ALT766)), active oxygen-eliminating agents (e.g., thioctic acid), and cerebral vasodilators (e.g., tiapride and mexiletine).

Examples of antihyperlipidemic agents include HMG-CoA reductase inhibitors (e.g., pravastatin sodium, simvastatin, lovastatin, atorvastatin calcium hydrate, fluvastatin sodium, itavastatin calcium, and rosuvastatin calcium), squalene synthetase inhibitors, ACAT inhibitors, cholesterol absorption inhibitors (e.g., ezetimibe), etc.

Examples of antihypertensive agents include angiotensin-converting enzyme inhibitors (e.g., captopril, enalapril maleate, alacepril, delapril hydrochloride, lisinopril, imidapril hydrochloride, benazepril hydrochloride, cilazapril hydrate, temocapril hydrochloride, and trandolapril), angiotensin II antagonists (e.g., olmesartan medoxomil, candesartan cilexetil, losartan potassium, pratosartan, valsartan, telmisartan, and irbesartan), calcium antagonists (e.g., nicardipine hydrochloride, manidipine hydrochloride, nisoldipine, nitrendipine, nilvadipine, and amlodipine besilate), ACE/NEP inhibitors (e.g., omapatrilat and fasidotril), β-blockers (e.g., atenolol, bisoprolol, betaxolol, and metoprolol), α-blockers (e.g., urapidil, terazosin, doxazosin, and bunazosin), αβ-blockers (e.g., amosulalol, arotinolol, labetalol, and carvedilol), renin inhibitors (e.g., aliskiren), aldosterone receptor antagonists (e.g., spironolactone and eplerenone), etc.

Examples of anti-obesity agents include central anti-obesity drugs (e.g., phentermine, sibutramine, amfepramone, dexamphetamine, mazindol, SR-141716A, cannabinoid receptor antagonists (e.g., rimonabant), opioid antagonists, opioid reuptake inhibitors, ghrelin antagonists, MCH receptor antagonists (e.g., SB-568849), neuropeptide Y antagonists, serotonin agonists, serotonin reuptake inhibitors, noradrenaline reuptake inhibitors, noradrenaline transporter inhibitors (e.g., S-2367 and CP-422935)), pancreatic lipase inhibitors (e.g., orlistat), peptide appetite suppressants (e.g., leptin and CNTF (ciliary neurotrophic factor)), cholecystokinin agonists, agouti-related peptide or protein function inhibitors, retinoid X receptor agonists, beta 2-adrenoceptor antagonists, beta 3 adrenoceptor agonists, diacylglycerol acyltransferase inhibitors, DPP4 inhibitors, fatty acid synthetase inhibitors, GSH receptor inhibitors, glucocorticoid receptor antagonists, glucokinase activators, histamine receptor agonists, IKK inhibitors, leptin receptor agonists, MTTP inhibitors, PPAR agonists, PPAR inhibitors, progesterone receptor agonists, SGLT-1 inhibitors, SGLT-2 inhibitors, stearoyl-CoA desaturase-1 (e.g., lintitript and FPL-15849), etc.

Examples of diuretics include xanthine derivatives (e.g., theobromine sodium salicylate and theobromine calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, and methyclothiazide), anti-aldosterone preparations (e.g., spironolactone and triamterene), carbonic anhydrase inhibitors (e.g., acetazolamide), chlorobenzene sulfonamide preparations (e.g., chlorthalidone, mefruside, and indapamide), azosemido, isosorbide, ethacrynic acid, piretanide, bumetanide, furosemide, etc.

Preferred examples of concomitant drugs include insulin preparations, insulin resistance improving agents, α-glucosidase inhibitors, biguanides, insulin secretagogues, DPPIV inhibitors, GLP-1, GLP-1 analogs, GLP-1 secretagogues, etc. These concomitant drugs can be used in combination of two or more at a suitable ratio.

When the compound of the present invention is used in combination with concomitant drugs, the amount of drugs used can be reduced within a safe range in terms of the side effects of the drugs. Accordingly, side effects presumably caused by such drugs can be safely prevented.

EXAMPLES

The present invention is described in detail with reference to Reference Examples and Examples, but is not limited to these examples. The identification of compounds was performed by using LC-MS spectroscopy, NRM spectroscopy, etc.

The silica gel chromatography used in Reference Examples and Examples is a silica gel SiOH produced by Yamazen Corporation. The purification conditions of the Gilson HPLC System were as follows: column: YMC Combi-Prep ODS-A, (S-5 µm, 12 nm, 20 mm×50 mm), flow rate: 35 mL/min, UV detection: 220 and 254 nm, elution solvent: A: 0.35% trifluoroacetic acid/acetonitrile, and B: 0.05% trifluoroacetic acid/water.

Reference Example 1

Production of ethyl 3-(4-aminophenyl)-2-furan carboxylate

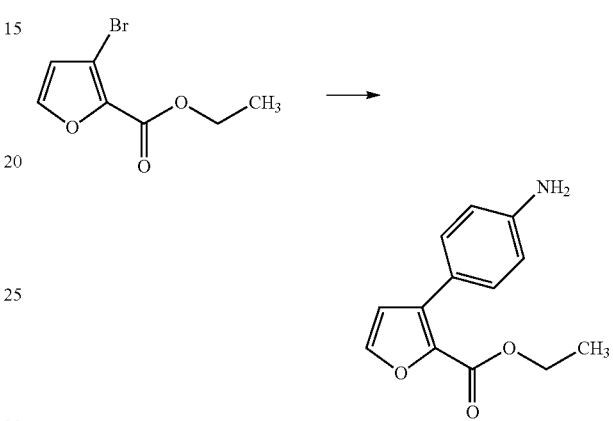

4-aminophenylboronic acid pinacol ester (40 g), tetrakis triphenylphosphine palladium (10.4 g), cesium carbonate (58.6 g), and water (50 mL) were added to a tetrahydrofuran (200 mL) solution of ethyl 3-bromo-2-furan carboxylate (26.3 g), and the mixture was heated at reflux for 48 hours under a nitrogen atmosphere. The organic layer of the reaction mixture was washed with a saturated sodium chloride solution, dried over magnesium sulfate, and concentrated under reduced pressure. The residue was subjected to column chromatography (ethyl acetate/hexane), thereby giving 27.4 g of a target compound as a solid.

The synthesis of ethyl 3-bromo-2-furan carboxylate was carried out according to the method described in Reference Example 1 of WO 03/064404.

$^1$H-NMR (300 MHz, CDCl$_3$) δ: 1.34 (t, J=7.2 Hz, 3H), 3.96 (brs, 2H), 4.34 (q, J=7.2 Hz, 2H), 6.59 (d, J=2.0 Hz, 1H), 6.74 (m, 2H) 7.46 (m, 2H), 7.53 (d, J=2.0 Hz, 1H)

Reference Example 2

Production of 3-(4-aminophenyl)-2-furancarboxylic acid hydrazide

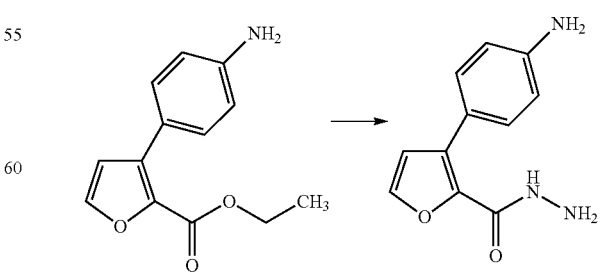

After ethyl 3-(4-aminophenyl)-2-furan carboxylate (7 g) was dissolved in a mixed solvent of 1,4-dioxane (7 mL) and ethanol (3 mL), hydrazine monohydrate (11.4 mL) was added. The mixture was heated at reflux for 6 hours. Ethyl acetate (100 mL) was added to the reaction mixture, and the mixture was washed with a saturated sodium chloride solution. Thereafter, the organic layer was dried over magnesium sulfate and concentrated under reduced pressure, thereby giving 3.8 g of the target compound as a solid.

$^1$H-NMR (400 MHz, DMSO-$d_6$) δ: 4.38 (s, 2H), 5.24 (s, 2H), 6.53 (m, 2H), 6.77 (d, J=2.0 Hz, 1H), 7.50 (m, 2H), 7.70 (d, J=2.0 Hz, 1H), 9.39 (s, 1H)

Reference Example 3

Production of 3-(4-aminophenyl)-2-furan carboxylic acid 2-(4-hydroxy-3-nitrobenzoyl)hydrazide hydrochloride

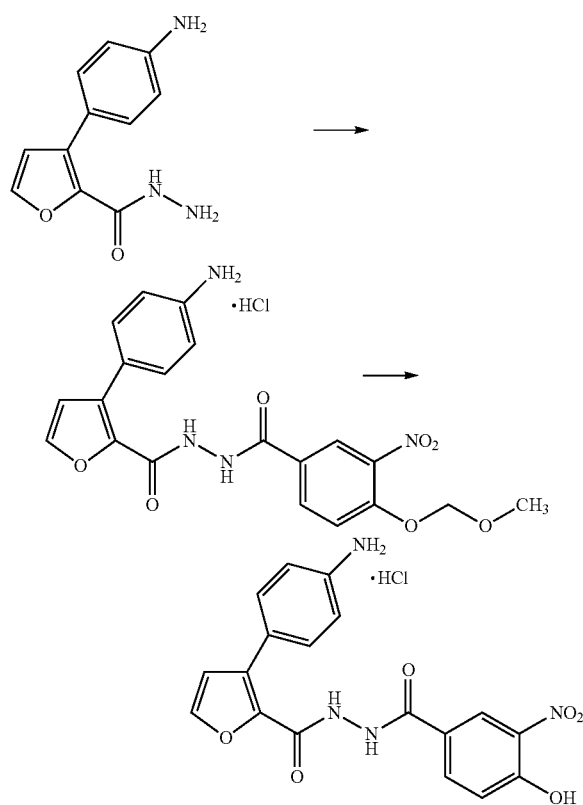

(1) After 3-(4-aminophenyl)-2-furan carboxylic acid hydrazide (5.9 g) was dissolved in a mixed solvent of dimethylformamide (50 mL) and tetrahydrofuran (50 mL), 4-methoxymethoxy-3-nitro benzoic acid (6.2 g) and 1-ethyl-3-(3-dimethylaminopropyl)carbodiimide hydrochloride (6.5 g) were added thereto. The mixture was stirred at room temperature all day and all night under a nitrogen atmosphere. Water (5 mL) was added to the reaction mixture, followed by extraction with ethyl acetate (150 mL). Thereafter, the organic layer was dried over magnesium sulfate and concentrated under reduced pressure. The residue was subjected to column chromatography (ethyl acetate/hexane). The resulting oily product was dissolved in ethyl acetate (150 mL), and 4 mol/L hydrochloric acid-ethyl acetate solution (15 mL) was added thereto. The mixture was stirred for 0.5 hours at room temperature, and a precipitated solid was collected by filtration. Ethyl acetate (10 mL) was added to the resulting solid, and the mixture was suspended and stirred for 0.5 hours, followed by collection by filtration, thereby giving 6.5 g of solid.

(2) A 4 mol/L hydrochloric acid-1,4-dioxane solution (11 mL) was added to a suspension of the solid (6.5 g), 2-propyl alcohol (60 mL), and tetrahydrofuran (60 mL), and the mixture was stirred at room temperature for 8 hours. After the reaction mixture was concentrated under reduced pressure, ethyl acetate (20 mL) was added to the residue. The mixture was stirred at room temperature for 1 hour, and the precipitated solid was collected by filtration. Ethyl acetate (10 mL) was added to the resulting solid, and the mixture was suspended and stirred for 0.5 hours. Thereafter, the precipitated solid was collected by filtration, thereby giving 4.5 g of a target compound as a solid.

$^1$H-NMR (400 MHz, DMSO-$d_6$) δ: 3.93 (s, 3H), 6.98 (d, J=2.2 Hz,1H), 7.27 (m, 2H), 7.27 (d, J=8.8 Hz,1H), 7.80 (m, 2H), 7.98 (d, J=2.2 Hz, 1H), 8.06 (dd, J=8.8, 2.2 Hz, 1H), 8.45 (d, J=2.2 Hz, 1H), 10.43 (s, 1H), 10.54 (s, 1H), 11.79 (br s, 1H)

Reference Example 4

Production of 1-(4-bromophenyl)-3,3-dimethoxy propan-1-one

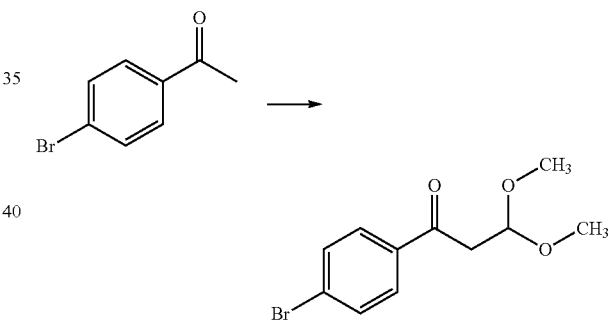

A tetrahydrofuran (206 mL) solution of 4-bromoacetophenone (61.4 g) and methyl formate (27.8 g) was added dropwise to a tetrahydrofuran (125 mL) suspension of sodium methoxide (25 g) under ice cooling, and the mixture was stirred at room temperature for 3 hours. The reaction mixture was added dropwise to a methanol sulfate solution (prepared by adding sulfuric acid (45.4 g) dropwise to methanol (150 mL) under ice cooling) at room temperature, and the mixture was stirred for 2 days. The reaction mixture was added dropwise at −5° C. to a 1 mol/L aqueous sodium hydroxide solution (925 mL), and then a 5 mol/L sulfuric acid aqueous solution was added thereto at the same temperature until the pH was 8. After ethyl acetate (500 mL) and water (500 mL) were added thereto, a 5 mol/L sulfuric acid aqueous solution was added at −5° C. until the pH was 8. The organic layer was separated and the water layer was extracted with ethyl acetate. Together with the organic layer, the water layer was sequentially washed with a 1 mol/L sodium chloride solution and a saturated sodium chloride solution, dried over magnesium sulfate, and concentrated under reduced pressure, thereby giving 80 g of a target compound as an oily product.

$^1$H-NMR (300 MHz, DMSO-d$_6$) δ: 3.41 (s, 6H), 3.24 (d, J=5.5 Hz, 2H), 4.97 (d, J=5.5 Hz, 1H), 7.61 (m, 2H), 7.82 (m, 2H)

Reference Example 5

Production of methyl 3-(4-bromophenyl)-2-furan carboxylate

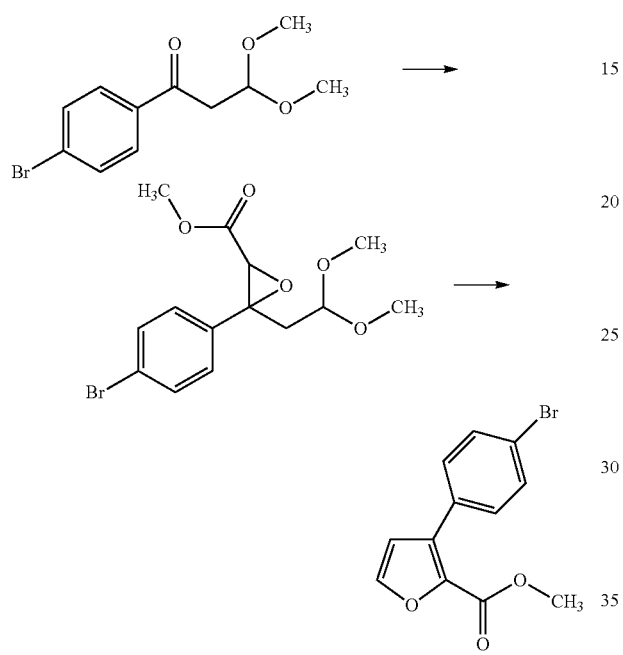

(1) Sodium methoxide (20.3 g) was added at −30° C. to a tetrahydrofuran (315 mL) solution of the target compound (57 g) of Reference Example 5 and chloro ethyl carbonate. The mixture was stirred at 0° C. for 2 hours, and then a 2 mol/L acetic acid aqueous solution was added to the reaction mixture until the pH was 6. Thereafter, the mixture was extracted with toluene. The organic layer was separated, and the water layer was extracted with toluene. Together with the organic layer, the water layer was sequentially washed with a saturated aqueous sodium hydrogen carbonate solution and a saturated sodium chloride solution, dried over magnesium sulfate, and concentrated under reduced pressure, thereby giving 80.8 g of oily product.

(2) p-toluene sulfonic acid (3.23 g) was added to a toluene (250 mL) solution of the aforementioned oily product (65.7 g), and the mixture was heated at reflux for 4 hours. After standing to cool, the reaction mixture was sequentially washed with a saturated aqueous sodium hydrogen carbonate solution and a saturated sodium chloride solution. The organic layer was dried over magnesium sulfate and concentrated under reduced pressure. The residue was subjected to column chromatography (chloroform), and water (153 mL) was added dropwise to a methanol (230 mL) solution of the resulting solid, and the mixture was stirred at 5° C. Thereafter, the precipitated crystals were collected by filtration and washed with a mixed solution of methanol and water, thereby giving 35.4 g of a target compound.

$^1$H-NMR (400 MHz, CDCl$_3$) δ: 3.86 (s, 3H), 6.61 (d, J=2.0 Hz, 1H), 7.46 (m, 2H) 7.54 (m, 2H), 7.58 (d, J =2.0 Hz, 1H)

Reference Example 6

Production of 3-(4-{[(1S)-1-(4-fluorophenyl)ethyl] amino}phenyl)-2-furancarboxylic acid hydrazide

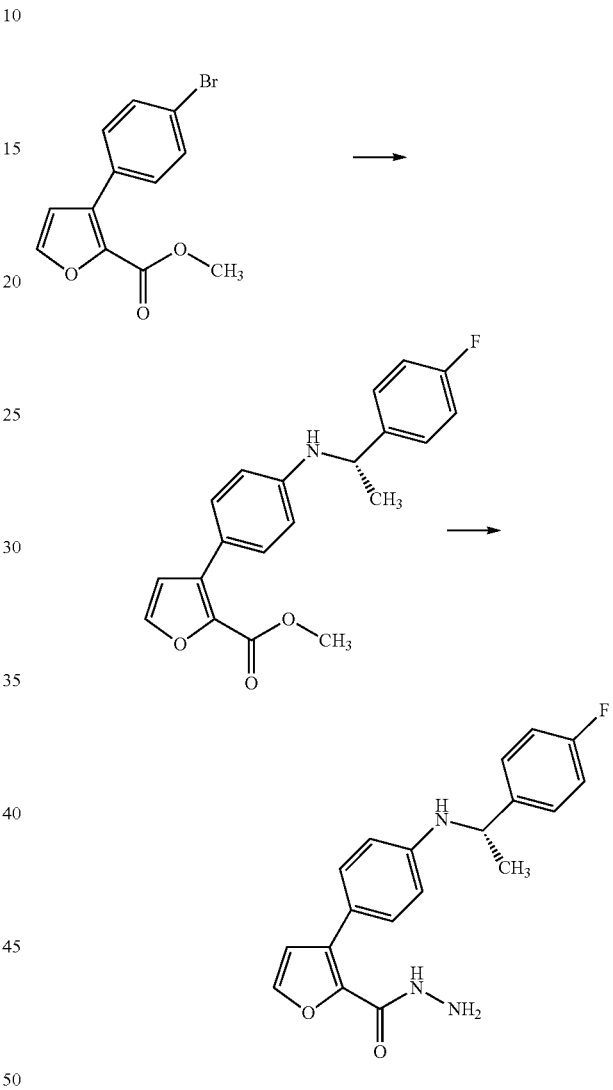

(1) A toluene solution (80 mL) of the target compound (2 g) of Reference Example 5, palladium acetate (0.1 g), rac-2,2'-bis(diphenylphosphino)-1,1'-binaphthyl (0.3 g), cesium carbonate (8.7 g), and (S)-4-fluoro-α-phenethylamine (1.5 g) was heated at 110° C. for 18 hours under a nitrogen atmosphere. After standing to cool to room temperature, the solution was filtered through celite, and the filtrate was concentrated under reduced pressure. The residue was subjected to column chromatography (ethyl acetate/hexane), thereby giving 1.5 g of a target compound as a yellow solid.

(2) In the same manner as in Reference Example 2, the oily product (1.5 g) was reacted and treated, thereby giving 1.5 g of a target compound as white amorphous substance.

$^1$H-NMR (400 MHz, DMSO-d$_6$) δ: 1.40 (d, J=6.6 Hz, 3H), 4.35 (s, 2H), 4.52 (quintet, J=6.6 Hz, 1H), 6.39 (d, J=6.6 Hz, 1H), 6.47 (m, 2H), 6.73 (d, J=2.0 Hz,1H), 7.10 (t, J=8.9 Hz, 2H), 7.40 (dd, J=8.8, 5.6 Hz, 2H), 7.47 (m, 2H), 7.68 (d, J=2.0 Hz,1H), 9.38 (s, 1H)

Reference Example 7

Production of 4-(methoxymethoxy)-3-nitro benzoic acid

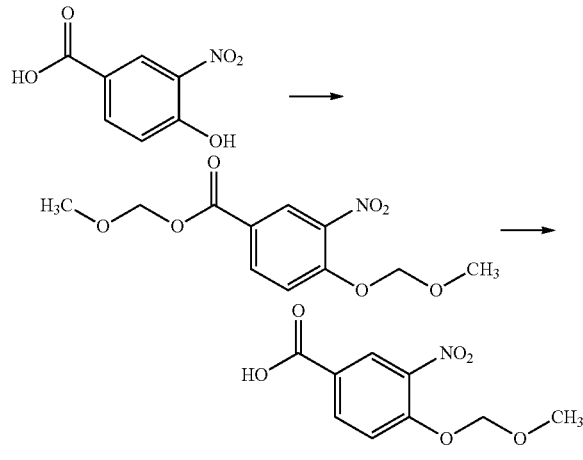

(1) Potassium carbonate (18.9 g) was added to an acetone (100 mL) solution of 4-hydroxy-3-nitro benzoic acid (10 g). Thereafter, methoxymethyl chloride (11 g) was added dropwise under ice cooling. Stirring was performed at room temperature for two hours, followed by suction filtration. The solid on a filter was washed with acetone (150 mL). The filtrate and the washing liquid were mixed, and concentrated under reduced pressure, thereby giving an oily product.

(2) A 4 mol/L aqueous sodium hydroxide solution (27.3 mL) was added dropwise to a methanol (50 mL) solution of the aforementioned oily product. The mixture was stirred at room temperature for 2 hours, and an aqueous potassium hydrogen sulfate solution was added to the reaction mixture. A precipitated solid was collected by filtration, and the solid was washed with water (300 mL). Thereafter, the solid was dried under reduced pressure at 70° C. for 8 hours, thereby giving 11.5 g of a target compound as a solid.

$^1$H-NMR (400 MHz, DMSO-$d_6$) δ: 3.41 (s, 3H), 5.44 (s, 2H), 7.50 (d, J=8.8 Hz, 1H), 8.15 (dd, J=8.8, 2.0 Hz, 1H), 8.33 (d, J=2.0 Hz, 1H), 13.33 (s, 1H)

Reference Example 8

Production of 3-cyano-4-hydroxy benzoic acid

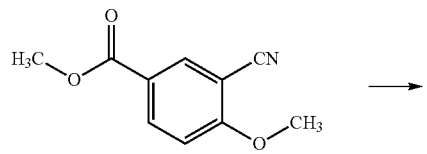

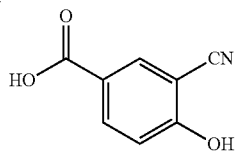

A mixture of methyl 3-cyano-4-methoxy benzoate (70 g) and hydrochloric acid pyridine (128.3 g) was stirred at 180° C. for 1 hour. Ice water (1 L) was added to the reaction mixture, and precipitated crystals were collected by filtration. Thereafter, recrystallization from ethyl acetate was performed, thereby giving 48.1 g of a target compound as a solid.

$^1$H-NMR (400 MHz, DMSO-$d_6$) δ: 7.08 (d, J=8.8 Hz, 1H), 8.02 (dd, J=8.8, 2.2 Hz, 1H), 8.09 (d, J=2.2 Hz, 1H), 11.97 (s, 1H), 12.99 (s, 1H)

Example 1

Production of 3-(4-{[1-(4-methylphenyl)ethyl]amino}phenyl)-2-furan carboxylic acid-2-(4-hydroxy-3-nitrobenzoyl)hydrazide hydrochloride

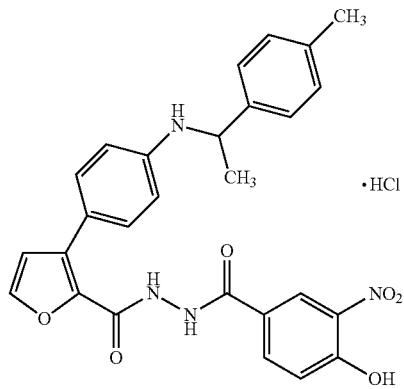

After a mixed solvent of methanol (4 mL) and acetic acid (0.5 mL) was added to the target compound (97.9 mg) of Reference Example 3, sodium acetate (30.1 mg) and 4-methylacetophenone (54.2 mg) were added. Subsequently, picoline borane (50.4 mg) was added, and the mixture was stirred at 40° C. for 5 hours. Ethyl acetate (20 mL) was added to the reaction mixture, and the mixture was washed with a saturated aqueous sodium hydrogen carbonate solution and a saturated sodium chloride solution. Thereafter, the organic layer was dried over magnesium sulfate and concentrated under reduced pressure. The residue was subjected to column chromatography (ethyl acetate/hexane). The residue obtained by concentrating the solvent under reduced pressure was dissolved in ethyl acetate, and 4 mol/L hydrochloric acid-ethyl acetate was added thereto, followed by stirring at room temperature. A precipitated solid was collected by filtration, thereby giving 62.2 mg of a target compound as a solid.

$^1$H-NMR (400 MHz, DMSO-$d_6$) δ: 1.49 (d, J=6.6 Hz, 3H), 2.22 (s, 3H), 4.58 (quintet, J=6.6 Hz, 1H), 4.94 (m, 2H), 6.83 (m, 2H), 6.89 (d, J=1.7 Hz, 1H), 7.09 (m, 2H), 7.25-7.32 (m, 2H), 7.25-7.32 (m, 1H), 7.61 (m, 2H), 7.88 (d, J=1.7 Hz,1H), 8.05 (dd, J=8.8, 2.2 Hz, 1H), 8.45 (d, J=2.2 Hz, 1H), 10.28 (s, 1H), 10.49 (s, 1H), 11.87 (s, 1H)

Examples 2 to 7

Reactions and treatments were carried out in the same manner as in Example 1 using the corresponding starting material compounds, thereby giving the compounds of Examples 2 to 7 shown in Table 1.

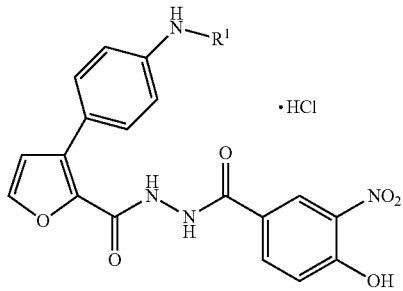

TABLE 1

| Example | —NHR¹ | LC-MS M + 1/Retention time (min) |
|---|---|---|
| 2 | (4-isopropylbenzyl)(methyl)amine structure | 529.2/1.23 |
| 3 | (4-tert-butylbenzyl)(methyl)amine structure | 544.3/1.26 |
| 4 | methyl(1-phenylethyl)amine structure | 501.2/1.11 |
| 5 | methyl(1-phenylpropyl)amine structure | 515.3/1.18 |
| 6 | (4-tert-butylphenyl)methyl(methyl)amine structure | 529.3/1.23 |
| 7 | N-methyl-[4-(trifluoromethoxy)benzyl]amine structure | 557.2/1.14 |

The conditions for chromatography of LC-MS were as follows: column: Waters ACQUITY UPLC BEH C18 (1.7 μm, 2.1 mm×50 mm), flow rate: 0.75 mL/min, UV detection: 220 and 254 nm, elution conditions: using A: 0.05% formic acid aqueous solution and B: 0.05% formic acid methanol solution as elution solvents, solution sending performed under the following conditions: 0.0-1.3 min, Linear gradient from B: 25% to 99%.

Example 8

Production of 3-{4-[4-(1-phenylethyl)amino]phenyl}-2-furan carboxylic acid-2-(4-hydroxy-3-nitrobenzoyl)hydrazide hydrochloride

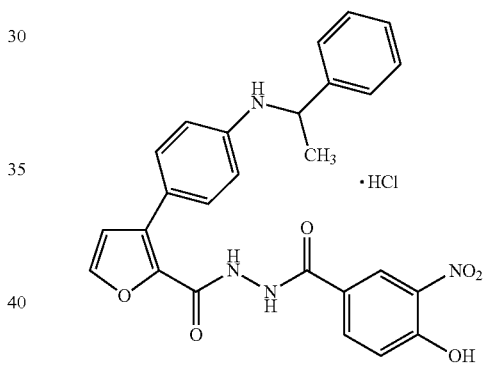

After a mixed solvent of methanol (1 mL) and acetic acid (0.5 mL) was added to the target compound (20.9 mg) of Reference Example 3, sodium acetate (49.6 mg) and acetophenone (10.2 mg) were added. Subsequently, picoline borane (26.7 mg) was added thereto, and the mixture was stirred at 40° C. for 5 hours. Ethyl acetate (5 mL) was added to the reaction mixture, and the mixture was washed with a saturated aqueous sodium hydrogen carbonate solution and a saturated sodium chloride solution. The organic layer was concentrated under reduced pressure. The residue was purified by using a Gilson HPLC System, and the residue obtained by concentrating the solvent under reduced pressure was dissolved in 1,4-dioxane. 4 mol/L hydrochloric acid-1, 4-dioxane (0.005 mL) was added thereto, and the mixture was concentrated under reduced pressure. 1,4-dioxane was added to the residue and freeze-dried, thereby giving 15.8 mg of a target compound as a solid.

LC-MS: 487.4 (M+1), 3.78 min (Retention time) The conditions for chromatography of LC-MS were as follows: column: Shiseido CAPCELL PAK C18 ACR (S-5 μm, 4.6 mm×50 mm), flow rate: 3.5 mL/min, UV detection: 220 and 254 nm, solution sending performed using elution solvents: A: 0.35% trifluoroacetic acid/ acetonitrile, and B: 0.05% trifluoroacetic acid/water at the following gradient: 0.0 to 0.5 min, A: 10%, 0.5-4.8 min, Linear gradient from A: 10% to 99%, 4.8-5.0 min, A: 99%.

Examples 9 to 67

Reactions and treatments were carried out in the same manner as in Example 8, using the corresponding starting material compounds, thereby giving the compounds of Examples 9 to 67 shown in Tables 2 to 6.

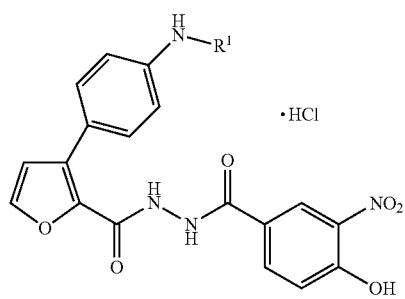

TABLE 2

| Example | —NHR¹ | LC-MS M + 1/Retention time (min) |
|---|---|---|
| 9 | | 515.6/4.06 |
| 10 | | 493.7/3.66 |
| 11 | | 505.5/3.87 |
| 12 | | 545.5/3.62 |
| 13 | | 501.7/3.92 |
| 14 | | 531.3/3.75 |
| 15 | | 515.5/4.06 |
| 16 | | 523.5/4.08 |
| 17 | | 523.5/4.12 |
| 18 | | 553.3/4.00 |
| 19 | | 527.5/4.16 |
| 20 | | 531.5/3.50 |
| 21 | | 522.5/3.00 |
| 22 | | 505.7/3.28 |

TABLE 3
| Example | —NHR¹ | LC-MS M + 1/Retention time (min) |
|---|---|---|
| 23 | 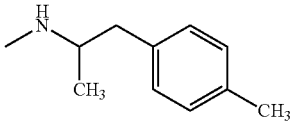 | 515.5/3.73 |
| 24 | 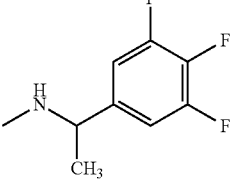 | 541.5/4.24 |
| 25 | 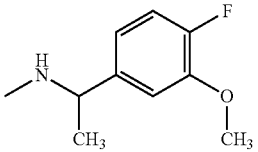 | 535.5/3.82 |
| 26 | 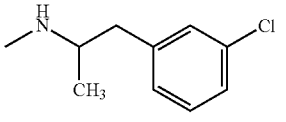 | 535.5/3.90 |
| 27 | 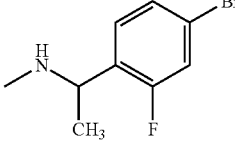 | 583.3/4.36 |
| 28 | 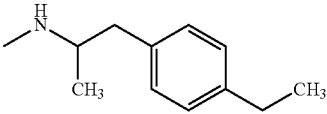 | 529.5/3.89 |
| 29 | 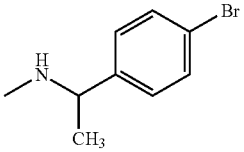 | 567.3/4.19 |
| 30 | 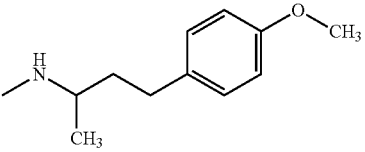 | 545.6/3.49 |
| 31 | 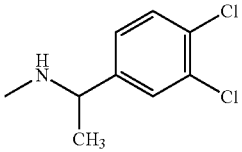 | 555.3/4.39 |
TABLE 3-continued
| Example | —NHR¹ | LC-MS M + 1/Retention time (min) |
|---|---|---|
| 32 | 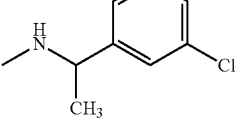 | 521.6/4.27 |
| 33 | 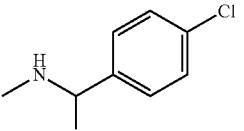 | 521.7/4.13 |
| 34 | 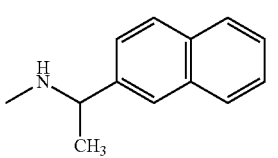 | 537.4/4.14 |
| 35 | 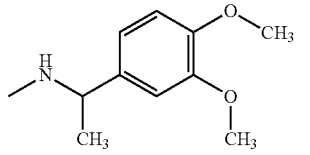 | 547.5/3.37 |
| 36 | 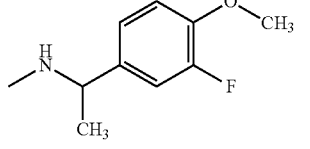 | 535.4/3.82 |
TABLE 4
| Example | —NHR¹ | LC-MS M + 1/Retention time (min) |
|---|---|---|
| 37 | 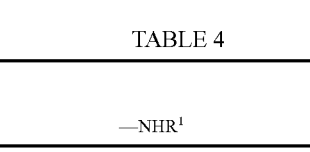 | 529.6/4.25 |
| 38 | 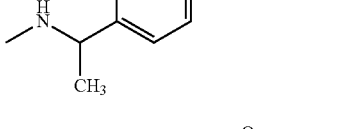 | 571.4/4.31 |
| 39 | 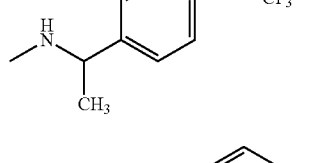 | 515.5/3.56 |

TABLE 4-continued
| Example | —NHR¹ | LC-MS M + 1/Retention time (min) |
|---|---|---|
| 40 | 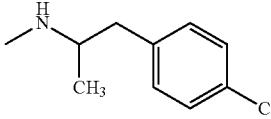 | 535.5/3.90 |
| 41 | 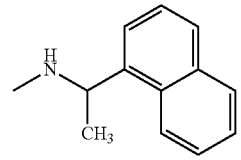 | 537.3/4.27 |
| 42 | 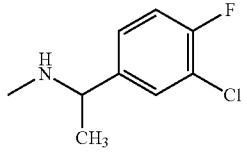 | 539.6/4.22 |
| 43 | 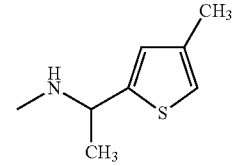 | 507.6/3.96 |
| 44 | 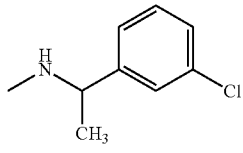 | 521.6/4.18 |
| 45 | 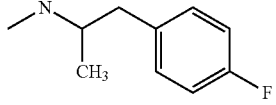 | 519.6/3.67 |
| 46 | 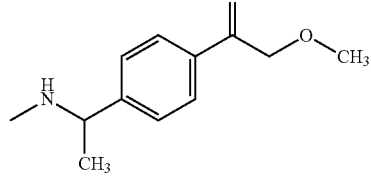 | 559.5/4.10 |
| 47 | 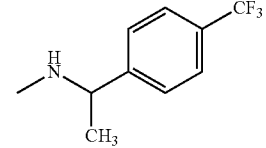 | 555.4/4.29 |
| 48 | 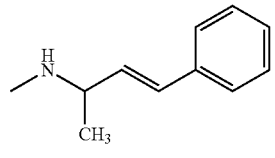 | 513.6/3.64 |
TABLE 4-continued
| Example | —NHR¹ | LC-MS M + 1/Retention time (min) |
|---|---|---|
| 49 | 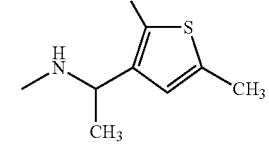 | 521.6/3.66 |
| 50 | 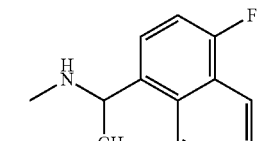 | 555.5/4.38 |
TABLE 5
| Example | —NHR¹ | LC-MS M + 1/Retention time (min) |
|---|---|---|
| 51 | 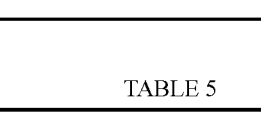 | 517.7/3.58 |
| 52 | 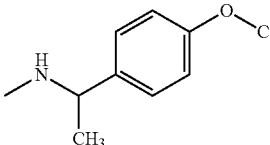 | 523.5/4.14 |
| 53 | 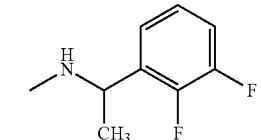 | 551.3/3.99 |
| 54 | 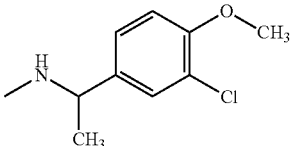 | 535.7/3.95 |
| 55 | 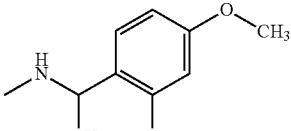 | 541.4/4.25 |
| 56 | 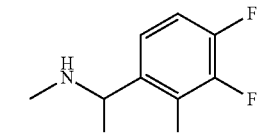 | 551.2/4.29 |

TABLE 5-continued

| Example | —NHR¹ | LC-MS M + 1/Retention time (min) |
|---|---|---|
| 57 | indanyl-CH(CH₃)-NH- | 527.7/4.08 |
| 58 | (2,4,5-trifluorophenyl)-CH(CH₃)-NH- | 541.4/4.22 |
| 59 | (4-fluoro-2-methoxyphenyl)-CH(CH₃)-NH- | 535.5/3.70 |
| 60 | benzothiophen-3-yl-CH(CH₃)-NH- | 543.2/4.16 |
| 61 | (2,5-dichlorothiophen-3-yl)-CH(CH₃)-NH- | 561.1/4.49 |
| 62 | (3,4-dimethylphenyl)-CH(CH₃)-NH- | 515.5/3.99 |
| 63 | (2-chloro-4-fluorophenyl)-CH(CH₃)-NH- | 539.6/4.35 |
| 64 | (4-chloro-3-methylphenyl)-CH(CH₃)-NH- | 535.5/4.29 |

TABLE 6

| Example | —NHR¹ | LC-MS M + 1/Retention time (min) |
|---|---|---|
| 65 | (4-methyl-3-fluorophenyl)-CH(CH₃)-NH- | 519.6/4.13 |
| 66 | (4-methyl-2,3-difluorophenyl)-CH(CH₃)-NH- | 537.5/4.30 |
| 67 | (4-chloro-2-fluorophenyl)-CH(CH₃)-NH- | 539.5/4.31 |

The conditions for chromatography of LC-MS were the same as for Example 8.

Example 68

Production of 3-(4-{[(1S)-1-(4-fluorophenyl)ethyl]amino}phenyl)-2-furan carboxylic acid-2-(4-hydroxy-3-nitrobenzoyl)hydrazide

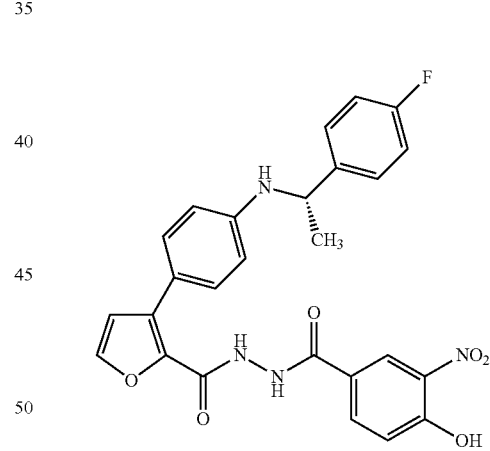

(1) 1-Ethyl-3-(3-dimethylaminopropyl)carbodiimide hydrochloride (1 g), 1-hydroxy benzotriazole (0.73 g), and triethylamine (0.9 mL) were added to a dimethylformamide (12 mL) solution containing the target compound (1.5 g) of Reference Example 6 and the target compound (1.1 g) of Reference Example 7, and the mixture was stirred at room temperature for 18 hours. Water was added to the reaction mixture, and then ethyl acetate was added thereto. The organic layer was sequentially washed with a saturated aqueous sodium hydrogen carbonate solution, water, and a saturated sodium chloride solution, then dried over magnesium sulfate, and concentrated under reduced pressure. The mixed solvent of methanol, diisopropylether, and hexane was added to the solid of the residue, followed by collection by filtration.

The solid was washed with the mixed solvent and then dried, thereby giving 2.1 g of yellow solid.

(2) A 4 mol/L hydrochloric acid-1,4-dioxane solution (8 mL) was added to a 2-propanol (5 mL) solution and a 1,4-dioxane (15 mL) mixed solution of the yellow solid (2.1 g), and the mixture was stirred at room temperature for 18 hours. The reaction mixture was concentrated under reduced pressure. After ethyl acetate and a saturated aqueous sodium hydrogen carbonate solution were added to the residue, 1 mol/L citric acid aqueous solution was added until the pH was 7 or less. The organic layer was separated and the water layer was extracted with ethyl acetate. Together with the organic layer, the water layer was washed with a saturated sodium chloride solution. The organic layer was dried and concentrated under reduced pressure. Acetonitrile was added to the residue, followed by stirring at room temperature. Precipitated crystals were collected by filtration, washed with acetonitrile, and dried, thereby giving 0.85 g of a target compound as an orange solid.

$^1$H-NMR (400 MHz, DMSO-$d_6$) δ: 1.40 (d, J=6.6 Hz, 3H), 4.53 (quintet, J=6.6 Hz, 1H), 6.49 (m, 1H), 6.49 (m, 2H), 6.85 (d, J=2.0 Hz,1H), 7.11 (t, J=8.9 Hz, 2H), 7.24 (d, J=8.8 Hz, 1H), 7.40 (dd, J=8.9, 5.6 Hz, 2H), 7.52 (m, 2H), 7.84 (d, J=2.0 Hz,1H), 8.06 (dd, J=8.8, 2.3 Hz, 1H), 8.47 (d, J=2.3 Hz, 1H), 10.20 (s, 1H), 10.46 (s, 1H), 11.78 (s, 1H)

Examples 69 to 79

Reactions and treatments were carried out in the same manner as in Example 68 using the corresponding starting material compounds, thereby giving the compounds of Examples 69 to 79 shown in Tables 7 to 8.

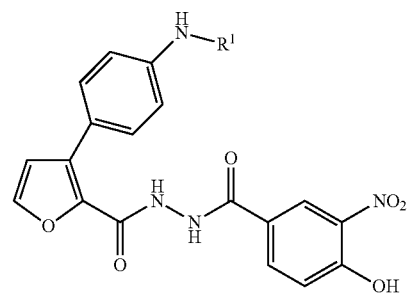

TABLE 7

| Example | —NHR$^1$ | $^1$H-NMR (400 MHz, DMSO-$d_6$) δ |
|---|---|---|
| 69 | (S)-N-methyl-1-(4-methylphenyl)ethylamine group | 1.38 (d, J = 6.6 Hz, 3H), 2.22 (s, 3H), 4.44 (quintet, J = 6.6 Hz, 1H), 6.38 (d, J = 6.6 Hz, 1H), 6.46 (m, 2H), 6.83 (d, J = 2.0 Hz, 1H), 7.07 (m, 2H), 7.20-7.28 (m, 1H), 7.20-7.28 (m, 2H), 7.49 (m, 2H), 7.82 (d, J = 2.0 Hz, 1H), 8.05 (dd, J = 8.8, 2.2 Hz, 1H), 8.45 (d, J = 2.2 Hz, 1H), 10.16 (s, 1H), 10.44 (s, 1H), 11.74 (s, 1H) |
| 70 | (S)-N-methyl-1-(4-ethylphenyl)ethylamine group | 1.14 (t, J = 7.6 Hz, 3H), 1.40 (d, J = 6.8 Hz, 3H), 2.52 (q, J = 7.6 Hz, 2H), 4.47 (quintet, J = 6.8 Hz, 1H), 6.51-6.44 (brs, 1H), 6.49 (m, 2H), 6.84 (d, J = 2.0 Hz, 1H), 7.12 (m, 2H), 7.24 (d, J = 8.8 Hz, 1H), 7.27 (m, 2H), 7.51 (m, 2H), 7.83 (d, J = 2.0 Hz, 1H), 8.06 (dd, J = 8.8, 2.2 Hz, 1H), 8.46 (d, J = 2.2 Hz, 1H), 10.19 (s, 1H), 10.46 (s, 1H), 11.78 (s, 1H) |
| 71 | (S)-N-methyl-1-(3,4-dimethylphenyl)ethylamine group | 1.38 (d, J = 6.8 Hz, 1H), 2.14 (s, 3H), 2.17 (s, 3H), 4.40 (quintet, J = 6.8 Hz, 1H), 6.37 (d, J = 6.8 Hz, 1H), 6.47 (m, 2H), 6.84 (d, J = 2.0 Hz, 1H), 7.08-7.00 (m, 1H), 7.15-7.11 (m, 1H), 7.23 (d, J = 8.8 Hz, 1H), 7.50 (m, 2H), 7.83 (d, J = 2.0 Hz, 1H), 8.06 (dd, J = 8.8, 2.2 Hz, 1H), 8.46 (d, J = 2.2 Hz, 1H), 10.18 (s, 1H), 10.45 (s, 1H), 11.70 (s, 1H) |
| 72 | (S)-N-methyl-1-(4-chlorophenyl)ethylamine group | 1.40 (d, J = 6.6 Hz, 3H), 4.53 (quintet, J = 6.6 Hz, 1H), 6.48 (d, J = 6.6 Hz, 1H), 6.48 (m, 2H), 6.85 (d, J = 2.0 Hz, 1H), 7.24 (d, J = 8.8 Hz, 1H), 7.34 (m, 2H), 7.40 (m, 2H), 7.52 (m, 2H), 7.83 (d, J = 2.0 Hz, 1H), 8.06 (1.0H, dd, J = 8.8, 2.2 Hz), 8.47 (d, J = 2.2 Hz, 1H), 10.46 (s, 1H), 10.19 (s, 1H), 11.78 (s, 1H) |
| 73 | (S)-N-methyl-1-(3-methylphenyl)ethylamine group | 1.40 (d, J = 6.6 Hz, 3H), 2.26 (s, 3H), 4.45 (quintet, J = 6.6 Hz 1H), 6.42 (d, J = 6.6 Hz, 1H), 6.49 (m, 2H), 6.85 (d, J = 1.7 Hz, 1H), 6.99 (m, 1H), 7.17 (m, 3H), 7.23 (d, J = 8.8 Hz, 1H), 7.51 (m, 2H), 7.83 (d, J = 1.7 Hz, 1H), 8.06 (dd, J = 8.8, 2.2 Hz, 1.1H), 8.47 (d, J = 2.2 Hz, 1H), 10.19 (s, 1H), 10.45 (s, 1H), 11.78 (s, 1H) |

TABLE 8

| Example | —NHR¹ | ¹H-NMR (400 MHz, DMSO-d₆) δ |
|---|---|---|
| 74 | (structure: N-methyl-(1-(4-chloro-2-fluorophenyl)ethyl)amine) | 1.43 (d, J = 6.6 Hz, 3H), 4.47 (quintet, J = 6.6 Hz, 1H), 6.46 (m, 2H), 6.51 (d, J = 6.6 Hz, 1H), 6.84 (d, J = 1.7 Hz, 1H), 7.21 (d, J = 8.5 Hz, 2H), 7.21 (m, 1H), 7.21 (m, 1H), 7.38 (m, 1H), 7.38 (m, 1H), 7.39 (m, 1H), 7.53 (m, 2H), 7.83 (d, J = 1.7 Hz, 1H), 8.04 (dd, J = 8.8, 1.7 Hz, 1H), 8.45 (d, J = 1.7 Hz, 1H), 10.19 (s, 1H), 10.44 (s, 1H), 11.78 (s, 1H) |
| 75 | (structure: N-methyl-(1-(4-chloro-3-methylphenyl)ethyl)amine) | 1.40 (d, J = 6.6 Hz, 3H), 2.29 (s, 3H), 4.47 (quintet, J = 6.6 Hz, 1H), 6.44 (d, J = 6.6 Hz, 1H), 6.48 (m, 2H), 6.84 (d, J = 2.0 Hz, 1H), 7.19-7.23 (m, 7.23 (d, J = 8.8 Hz, 1H), 7.31 (d, J = 8.0 Hz, 1H), 7.34-7.36 (m, 1H), 7.52 (m, 2H), 7.83 (d, J = 2.0 Hz, 1H), 8.05 (dd, J = 8.8, 2.2 Hz, 1H), 8.47 (d, J = 2.2 Hz, 1H), 10.19 (s, 1H), 10.45 (s, 1H), 11.77 (s, 1H) |
| 76 | (structure: N-methyl-(1-(4-fluorophenyl)ethyl)amine) | 1.39 (d, J = 6.6 Hz, 3H), 4.52 (quintet, J = 6.6 Hz, 1H), 6.44 (d, J = 6.6 Hz 1H), 6.47 (m, 2H), 6.83 (d, J = 1.7 Hz, 1H), 7.09 (t, J = 8.8 Hz, 2H), 7.22 (d, J = 8.8 Hz, 18), 7.39 (dd, J = 8.8, 5.6 Hz, 2H), 7.50 (m, 2H), 7.82 (d, J = 2.0 Hz, 1H), 8.05 (dd, J = 8.8, 2.3 Hz, 1H), 8.45 (d, J = 2.3 Hz, 1H), 10.17 (s, 1H), 10.44 (s, 1H), 11.75 (s, 1H) |

Examples 77 to 79

Using the corresponding starting material compounds, an amorphous substance obtained by the same reaction and treatment performed in Example 68 was dissolved in ethyl acetate. mol/L hydrochloric acid-ethyl acetate was added thereto, followed by stirring at room temperature. Precipitated crystals were collected by filtration, thereby giving the compounds of Examples 77 to 78 shown in Table 9.

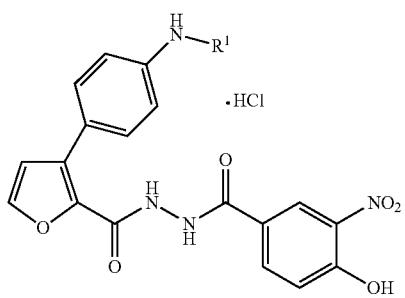

TABLE 9

| Example | —NHR¹ | ¹H-NMR (400 MHz, DMSO-d₆) δ |
|---|---|---|
| 77 | (structure: N-methyl-(1-cyclohexyl)ethyl)amine) | 0.90-1.30 (m, 6H), 1.09 (d, J = 6.6 Hz, 3H), 1.40-1.90 (m, 5H), 4.13 (m, 1H), 6.95 (m, 1H), 7.02 (m, 2H), 7.27 (d, J = 8.5 Hz, 1H), 7.73 (m, 2H), 7.92 (m, 1H), 8.06 (dd, J = 8.8, 2.2 Hz, 1H), 8.46 (d, J = 2.2 Hz, 1H), 10.32 (s, 1H), 10.51 (s, 1H), 11.85 (s, 1H) |

TABLE 9-continued

| Example | —NHR¹ | ¹H-NMR (400 MHz, DMSO-d₆) δ |
|---|---|---|
| 78 | (structure: N-methyl-(1-phenyl)ethyl)amine) | 1.46 (d, J = 6.6 Hz, 3H), 4.57 (quintet, J = 6.6 Hz, 1H), 6.65 (m, 2H), 6.87 (d, J = 2.0 Hz, 1H), 7.20 (t, J = 7.8 Hz, 1H), 7.26 (d, J = 8.8 Hz, 1H), 7.30 (t, J = 7.8 Hz, 2H), 7.40 (d, J = 7.8 Hz, 2H), 7.56 (d, J = 8.0 Hz, 2H), 7.86 (d, J = 2.0 Hz, 1H), 8.06 (dd, J = 8.8, 2.2 Hz, 1H), 8.46 (d, J = 2.2 Hz, 1H), 10.24 (s, 1H), 10.48 (s, 1H), 11.84 (s, 1H) |

Example 79

Production of 3-(4-{[(1S)-1-(4-fluorophenyl)ethyl]amino}phenyl)-2-furan carboxylic acid-2-(3-cyano-4-hydroxybenzoyl)hydrazide

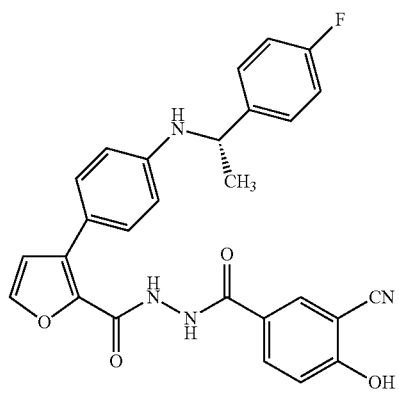 [SMILES: C[C@H](Nc1ccc(-c2ccoc2C(=O)NNC(=O)c2ccc(O)c(C#N)c2)cc1)c1ccc(F)cc1]

Thionyl chloride (0.89 g) was added to an ethyl acetate (5 mL) solution of 3-cyano-4-hydroxy benzoic acid (0.41 g), and the mixture was heated at reflux for 2 hours. The reaction mixture was concentrated under reduced pressure and subjected to azeotropic distillation of ethyl acetate and tetrahydrofuran. Thereafter, the residue was dissolved in tetrahydrofuran (5 mL), and added dropwise to a tetrahydrofuran (5 mL) solution of the target compound (0.85 g) of Reference Example 6 under ice cooling. The resultant was stirred at room temperature all day and all night, and then an aqueous sodium hydroxide solution (5 mL) was added thereto under ice cooling. The mixture was stirred at the same temperature for 30 minutes. A 1 mol/L citric acid aqueous solution was added to the reaction mixture until the pH was 7 or less, and extraction with ethyl acetate was performed. The organic layer was washed with a saturated sodium chloride solution, and then concentrated under reduced pressure. The residue was subjected to column chromatography (chloroform/methanol), and ethyl acetate recrystallization, thereby giving 0.81 g of a target compound as a solid.

$^1$H-NMR (400 MHz, DMSO-d$_6$) δ: 1.39 (d, J=6.6 Hz, 3H), 4.52 (quintet, J=6.6 Hz, 1H), 6.43 (d, J=6.6 Hz, 1H), 6.47 (m, 2H), 6.83 (d, J=2.0 Hz,1H), 7.09 (t, J=8.9 Hz, 2H), 7.09 (d, J=8.9 Hz, 1H), 7.39 (dd, J=8.9, 5.9 Hz, 2H), 7.51 (m, 2H), 7.82 (d, J=2.0 Hz,1H), 8.02 (dd, J=8.9, 2.2 Hz, 1H), 8.15 (d, J=2.2 Hz, 1H), 10.14 (s, 1H), 10.30 (s, 1H), 11.86 (s, 1H)

Effects of the compound of the present invention that support the value as a glucogon receptor antagonist are explained with reference to the Experiments shown below.

Experiment 1—Experiment for Glucagon Receptor Binding Inhibition—

The composition of the reaction solution used in the receptor binding inhibition experiment was prepared according to the method described in Bioorg. Med. Chem. Lett., 1992, 12, 915-918, using the following methods. ($_3$-[$^{125}$I] iodotyrosyl$^{10}$) Glucagon and a rat hepatocyte membrane were obtained or prepared according to the following methods.

(3-[$^{125}$I] iodotyrosyl$^{10}$)Glucagon was obtained according to the following method at PerkinElmer Co., Ltd (Great Britain). Using a chloramine T method, glucagon (Peptide Institute) was labeled with [$^{125}$I], and (3-[$^{125}$I] iodotyrosyl$^{10}$)Glucagon was separated using HPLC. Purchased from PerkinElmer Co., Ltd. (Great Britain), was a product obtained by dissolving it in an aqueous solution containing 10 mM citric acid, 5% lactose, 0.2% cysteine HCl, and 0.25% BSA so that the radioactivity was 3.7 MBq/mL at reference date, followed by freeze-drying. The product was re-dissolved in a 0.3-TIU/mL aprotinin aqueous solution so that the radioactivity was 3.7 MBq/mL at reference date, and it was freeze-stored at −15 to −40° C. for use.

A cell membrane was prepared from the liver of an SD rat according to the method described on pages 31 to 33 of Zikken Seibutsugaku Kouza 6, Saibou bunkakuhou (Experimental Biology Lecture 6, Cell Fraction Method) (Maruzen Co., Ltd.). The resulting cell membrane was freeze-stored at −70 to −85° C. for use.

The cell membrane that had been dissolved at room temperature and then suspended using a Physcotron (Microtec Co., Ltd. was added to a 50-mM Tris-HCl buffer (pH 7.2) containing 1 mg/mL BSA (Sigma-Aldrich), 0.1 mg/mL bacitracin (Wako Pure Chemical Industries, Ltd.), 1% DMSO, 0.01% acetic acid, and 50 pM) (3-[$^{125}$I] iodotyrosyl$^{10}$) Glucagon (pH 7.2) (each value indicating the final concentration and the radioactivity of (3-[$^{125}$I] iodotyrosyl$^{10}$) Glucagon calculated on the measurement date) to give a total amount of 0.2 mL. The reaction was started and incubation was performed at 25° C. for 120 minutes. The concentration of the cell membrane was adjusted so that 10% of the added)(3-[$^{125}$I] iodotyrosyl$^{10}$ Glucagon was equal to the total amount of binding.

Using a GF/C filter (Whatman International Ltd., Great Britain) immersed for more than 15 minutes in 0.3% polyethyleneimine (Sigma-Aldrich, Co., LLC), whose pH was adjusted to 7.2 by adding hydrochloric acid, the reaction solution was subjected to suction filtration to recover (3-[$^{125}$I] iodotyrosyl)Glucagon bound to the membrane. The filter was washed 3 times with an ice-cooled 50-mM Tris-HCl buffer (pH 7.4), and the radioactivity of the filter was measured by using a γ counter (1470 WIZARD γ-counter)(Wallac). The amount of specific binding was measured by subtracting the amount of nonspecific binding determined in the presence of 10 μM glucagon (Peptide Institute, Inc.) from the total amount of binding.

The amount of specific binding in the absence of a test compound was regarded as 100%, and inhibitions (%) at various concentrations of test compounds were calculated. The concentration at 50% inhibition of binding (IC$_{50}$) was calculated using a nonlinear least squares method. The results of glucagon receptor binding inhibitory activity are shown in Table 10 below.

TABLE 10

| Test compound | IC$_{50}$ (nM) Rat |
|---|---|
| Example 1 | 0.22 |
| Example 2 | 0.093 |
| Example 3 | 0.057 |
| Example 6 | 0.13 |
| Example 7 | 0.34 |
| Example 68 | 0.11 |
| Example 69 | 0.085 |
| Example 70 | 0.13 |
| Example 71 | 0.043 |
| Example 72 | 0.14 |
| Example 73 | 0.16 |
| Example 75 | 0.12 |
| Example 76 | 5.8 |
| Example 77 | 0.35 |
| Example 78 | 0.62 |
| Example 79 | 0.74 |
| Compound A | 2800 |
| Compound B | 1200 |
| Compound C | 340 |
| Compound D | 400 |
| Compound E | 9800 |

The compounds of the present invention exhibit strong glucagon receptor binding activity compared to the compounds A to E of Patent Literature 1 as mentioned above.

Experiment 2—Experiment for Glucagon Stimulation—

Crl: CD (SD) rats (male, 6 to 7 weeks old, n=8, Charles River Japan Inc.) and Nosan: Beagle dogs (male, 2-3 years old, n=3, Narc Corporation) were used in the experiment.

The inhibitory effects of the compounds of the present invention on the blood sugar increase caused by glucagon stimulation (0.3-10 μg/kg, sc/iv administration) were examined based on the blood sugar level. In each test using rats or dogs, glucagon was stimulated two hours after forced oral administration of either a solvent (methyl cellulose) or a drug suspension. The area under the blood concentration-time curve after glucagon stimulation, or the blood sugar level 15 minutes after administration were measured, and the effects were compared. The blood sugar level was calculated by a mutarotase glucose oxidase method. The results confirmed that the compounds of the present invention exhibit remarkable inhibitory effects on the blood sugar increase caused by glucagon stimulation compared to the compounds A to E.

Experiment 3: —Experiment for Blood Sugar Decrease—

Effects of the compound of Example 69 on hyperglycemia and impaired fasting glycemia in ob/ob mice, which are type II diabetes models, were examined.

B6.V-Lepob/J (ob/ob) mice and control B6.V-Lepob/J (?/+) mice (male, 6 to 7 weeks old, n=8, Charles River Japan Inc.) were used. To examine the effect on hyperglycemia, feed was removed from the cage at the same time as the start of drug administration, and to examine the effect on impaired fasting glycemia, feed was removed from the cage about 20 hours before the scheduled time of drug administration. Under each experimental condition, the mice were allowed free access to drinking water. 2, 4 and 6 hours after the forced oral administration of the compound (0.01-1.0 mg/kg) of Example 69, which had been suspended in 0.5% methyl cellulose, the blood sugar levels were examined. Under each experimental condition, the compound of Example 69 exhibited a remarkable blood sugar decreasing effect at any administration dosage at 2 hours after the administration. However, the blood sugar level was not reduced to below the level of the healthy mouse, which is control for pathology. The blood sugar decreasing effect attained by the high-dose administration continued even 6 hours after the administration.

Experiment 4: —Experiment of Combination use of Glucagon Receptor Antagonist and DPPIV Inhibitor—

An experiment using the compound of Example 69 and sitagliptin (DPPIV inhibitor) in combination was performed to examine the effect on postprandial hyperglycemia in ob/ob mice.

B6.V-Lepob/J (ob/ob) mice and control B6.V-Lepob/J (?/+) mice (male, 6 to 7 weeks old, n=8, Charles River Japan) were used. The compound of Example 69 suspended in 0.5% methyl cellulose (0.1 mg/kg) and sitagliptin (5 mg/lm) were orally administered to a mouse singly or in combination for a single time. One hour later, liquid food (ensure H, Abbott Japan, Co., Ltd., 1.5 kcal/mL) was orally administered. The blood sugar levels immediately before, and 15, 30, 60, and 90 minutes after administration of the liquid food were measured.

The comparison of the area under the blood concentration-time curve confirmed abnormal saccharometabolism in the ob/ob mice. Regarding the abnormal saccharometabolism, although the single use of the compound of Example 69 or sitagliptin normalized the area under the blood concentration-time curve, it could not normalize the blood sugar increase 15 minutes after the administration of liquid food. In contrast, the combination use of these agents normalized the area under the blood concentration-time curve and the blood sugar level 15 minutes after the administration of liquid food without causing hypoglycemia.

Figure 1:
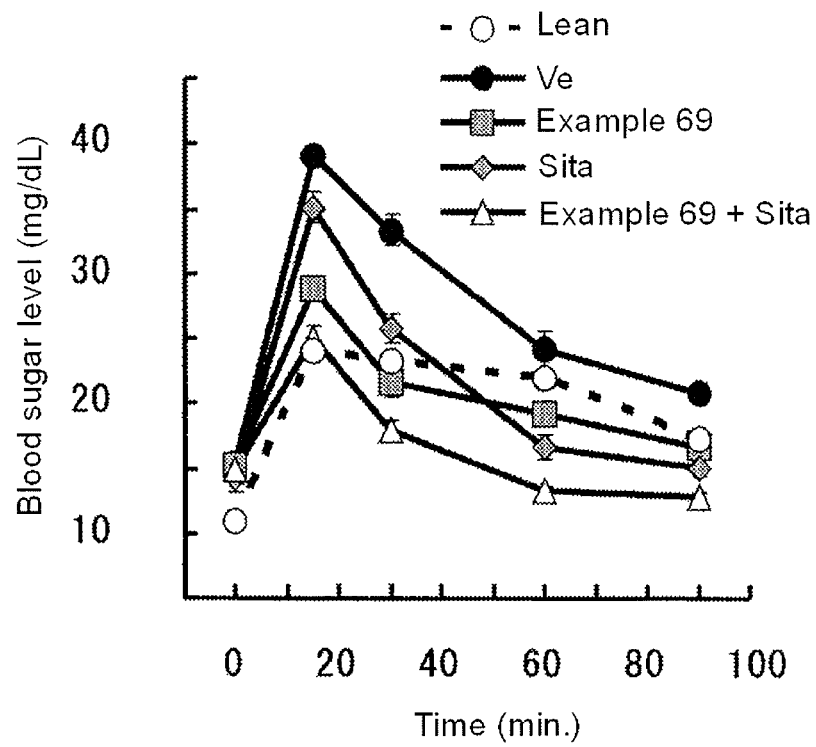
FIG. 1 shows the influence of a single-dose administration of a compound of Example 69 in combination with sitagliptin (Sita) on postprandial hyperglycemia in ob/ob mice. Changes with time in blood sugar levels are shown. The data is presented as average values±standard error.
Figure 2:
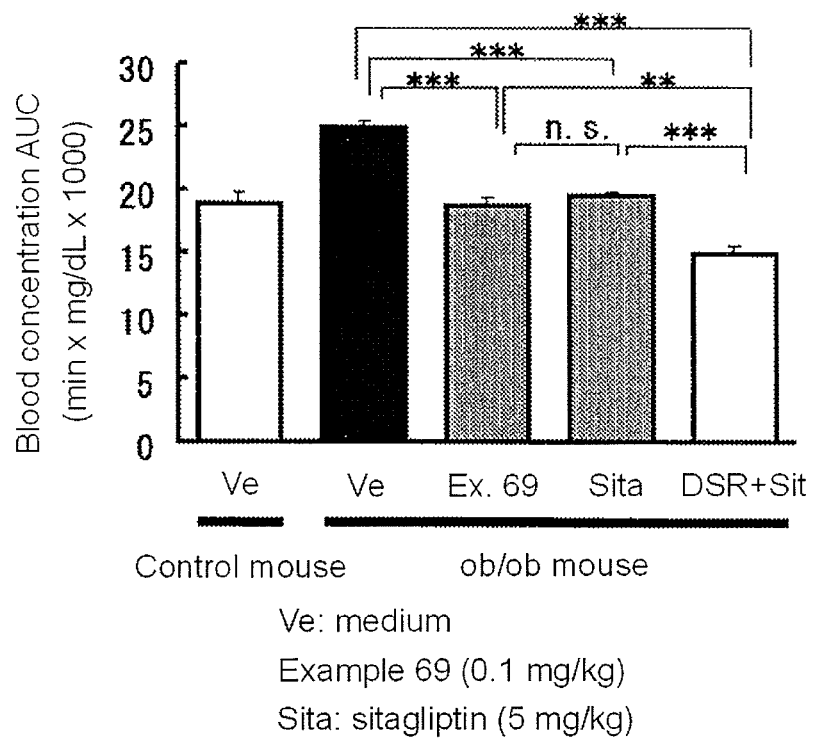
FIG. 2 shows the influence of a single-dose administration of the compound of Example 69 in combination with sitagliptin (Sita) on postprandial hyperglycemia in ob/ob mice. The area under the blood concentration-time curve (AUC) is shown. The data is presented as average values±standard error.

Accordingly, it was revealed that the combination use of the agents exhibit an extremely stronger postprandial hyperglycemia inhibitory effect than the single use of each agent (FIGS. 1 and 2).

Experiment 5: —Experiment of Combination use of Glucagon Receptor Antagonist and Metformin—

An experiment using the compound of Example 69 and metformin in combination was performed to examine the effect on the HbAlc value in ob/ob mice.

B6.V-Lepob/J (ob/ob) mice and control B6.V-Lepob/J (?/+) mice (male, 6 to 7 weeks old, n=8, Charles River Japan) were used. The compound of Example 69 (3 mg/kg, twice a day) suspended in 0.5% methyl cellulose, and metformin (100 mg/kg, twice a day) dissolved in the solvent were orally administered repeatedly for 4 weeks singly or in combination.

The effects were compared based on the hemoglobin A1 (HbAlc) value, and a diabetes-like state (prolonged hyperglycemic state) was confirmed by HbAlc increase in the ob/ob mice. Regarding the HbAlc increase, the single use of the compound of Example 69 or metformin resulted in HbAlc reduction. The combination use of these agents showed a higher HbAlc reduction effect.

The results reveal that the combination use of these agents exhibits an extremely stronger HbAlc reduction effect than the single use of each agent (FIG. 3).

Experiment 6: —Experiment of Combination use of Glucagon Receptor Antagonist and PPAR Activating Agent—

An experiment using the compound of Example 69 and pioglitazone in combination was performed to examine the effect on the HbAlc values in ob/ob mice.

B6.V-Lepob/J (ob/ob) mice and control B6.V-Lepob/J (?/+) mice (male, 6 to 7 weeks old, n=8, Charles River Japan) were used. The compound of Example 69 suspended in 0.5% methyl cellulose (3 mg/kg, twice a day), and pioglitazone (1 mg/kg, once a day) were orally administered repeatedly for 4 weeks singly or in combination.

The effects were compared based on the hemoglobin A1 (HbA1c) value, and a diabetes-like state (prolonged hyperglycemic state) was confirmed by HbA1c increase in the ob/ob mice. Regarding the HbAlcHbA1c increase, although the compound of Example 69 attained HbA1c reduction, the HbA1c reduction effect of the pioglitazone was not confirmed under the current experimental conditions. However, the combination use of these agents showed a higher HbA1c reduction effect than the single use of the compound of Example 69.

The results reveal that the combination use of these agents exhibits an extremely stronger HbA1c reduction effect than the single use of each agent (FIG. 4).

Industrial Applicability

The compound of the present invention exhibits potent glucagon receptor antagonistic activity and can be used in the prevention and/or treatment of symptoms and diseases in which glucagon is involved, such as hyperglycemia, abnormal glucose tolerance, insulin resistance syndrome, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, metabolic syndrome, diabetic complications (cataracts, retinopathy, keratopathy, neuropathy, nephropathy, peripheral circulatory failure, cerebrovascular disorder, ischemic heart disease, arteriosclerosis, etc.), and other such symptoms and diseases.

The invention claimed is:

1. A compound represented by Formula (II) or a pharmaceutically acceptable salt thereof:

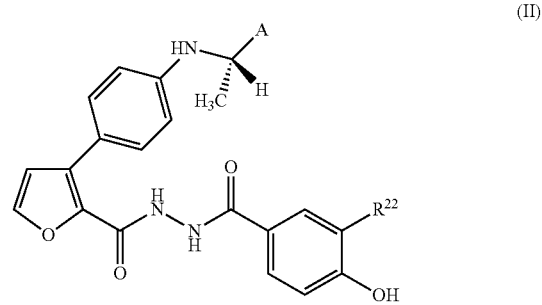

wherein A is one member selected from the group consisting of groups represented by Formulae (a) to (d) below:

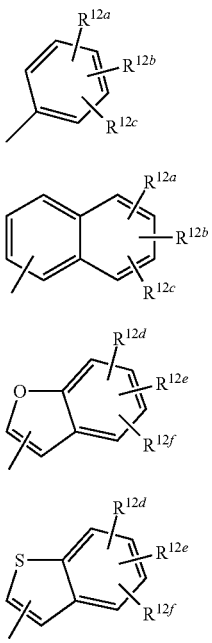

wherein $R^{12a}$, $R^{12b}$, and $R^{12c}$ are the same or different, and independently represent:
1: a hydrogen atom,
2: a halogen atom,
3: a $C_{1-4}$ alkyl group, which is optionally substituted with 1 to 3 fluorine atoms,
4: a $C_{1-4}$ alkoxy group, which is optionally substituted with 1 to 3 fluorine atoms, or
5: a $C_{1-4}$ alkylcarbonyl group, which is optionally substituted with $C_{1-4}$ alkoxy;

$R^{12d}$, $R^{12e}$, and $R^{12f}$ are the same or different, and independently represent:
1: a hydrogen atom,
2: a halogen atom, or
3: $C_{1-4}$ alkyl; and
$R^{22}$ is a cyano group or a nitro group.

2. The compound according to claim 1, or a pharmaceutically acceptable salt thereof, wherein A is a methylphenyl group.

3. The compound according to claim 1, or a pharmaceutically acceptable salt thereof, wherein A is a ethylpheny group.

4. The compound according to claim 1, or a pharmaceutically acceptable salt thereof, wherein A is a 4-(2 propyl) phenyl group.

5. The compound according to claim 1, or a pharmaceutically acceptable salt thereof, wherein A is a 4-(1,1,1-trimrthylmethyl)phenyl group.

6. The compound according to claim 1, or a pharmaceutically acceptable salt thereof, wherein $R^{22}$ is a cyano group.

7. The compound according to claim 1, or a pharmaceutically acceptable salt thereof, wherein $R^{22}$ is a nitro group.

8. The compound according to claim 1 selected from a compound group below, or a pharmaceutically acceptable salt thereof, the compound group consisting of:
3-{4-[((1S)-1-phenylethyl)amino]phenyl}-2-furancarboxylic acid-2-(4-hydroxy-3-nitrobenzoyl)hydrazide,
3-(4-{[(1S)-1-(3-methylphenyl)ethyl]amino}phenyl)-2-furancarboxylic acid-2-(4-hydrox)-3-nitrobenzoyl)hydrazide,
3-(4-{[(1S)-1-(4-ethylphenyl)ethyl]amino}phenyl)-2-furancarboxylic acid-2-(4-hydroxy)-3-nitrobenzoyl) hydrazide,
3-(4-{[(1S)-1-(4-chlorophenyl)ethyl]amino}phenyl)-2-furancarboxylic acid-2-(4-hydroxy-3-nitrobenzoyl)hydrazide,
3-(4{[(1S)-1-(3,4-dimethylphenyl)ethyl ]amino}phenyl)-2-furancarboxylic acid-2-(4-hydroxy)-3-nitrobenzoyl) hydrazide,
3-(4{[(1S)-1-cyclohexylethyl]amino}phenyl)-2-furancarboxylic acid-2-(4-hydroxy-3-nitrobenzoyl)hydrazide,
3-(4-{[(1S)-1-(4-chloro-3-methylphenyl)ethyl] amino}phenyl)-2-furancarboxylic acid-2-(4-hydroxy-3-nitrobenzoyl)hydrazide,
3-(4-{[(1S)-1-(4-chloro-2-fluorophenyl)ethyl] amino}phenyl)-2-furancarboxylic acid-2-(4-hydroxy-3-nitrobenzoyl)hydrazide,
3-(4-{[(1S)-1-(4-fluorophenyl)ethyl]amino}phenyl)-2-furancarboxylic acid-2-(4-hydroxy-3-nitrobenzoyl)hydrazide, and
3-(4-{[(1S)-1-(4-methylphenyl)ethyl]amino}phenyl)-2-furancarboxylic acid-2-(4-hydroxy-3-nitrobenzoyl)hydrazide.

9. The compound according to claim 1 or a pharmaceutically acceptable salt thereof, the compound is
3-(4{[(1S)-1-(4-methylphenyl)ethyl]amino}phenyl)-2-furancarboxylic acid-2-(4-hydroxy-3-nitrobenzoyl)hydrazide.

10. The compound according to claim 1, or a pharmaceutically acceptable salt thereof, wherein $R^{22}$ is a nitro group.

11. A pharmaceutical composition comprising the compound according to claim 1 or a pharmaceutically acceptable salt thereof.

12. The compound according to claim 1, or a pharmaceutically acceptable salt thereof, the compound is
3-(4{[(1S)-1-(3,4-dimethylphenyl)ethyl]amino}phenyl)-2-furancarboxylic acid-2-(4-hydroxy-3-nitrobenzoyl) hydrazide.

13. The compound according to claim 1, or a pharmaceutically acceptable salt thereof, the compound is
3-(4-{[(1S)-1-(4-fluorophenyl)ethyl]amino }phenyl)-2-furancarboxylic acid-2-(4- hydroxy-3-nitrobenzoyl)hydrazide.

14. The compound according to claim 1, or a pharmaceutically acceptable salt thereof, wherein A is represented by Formula (a) below:

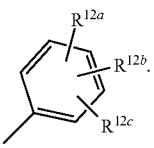

(a)

15. The compound according to claim 14, or a pharmaceutically acceptable salt thereof, wherein $R^{12a}$, $R^{12b}$, and $R^{12c}$ are the same or different, and independently represent a hydrogen atom or a $C_{1-4}$ alkyl optionally substituted with 1 to 3 fluorine atoms.

16. The compound according to claim 15, or a pharmaceutically acceptable salt thereof, wherein $R^{12a}$, $R^{12b}$, and $R^{12c}$ are the same or different, and independently represent a hydrogen atom, a methyl, an ethyl, a 2-propyl, or a 1,1,1-trimethylmethyl.

17. A compound represented by Formula (III) or a pharmaceutically acceptable salt thereof:

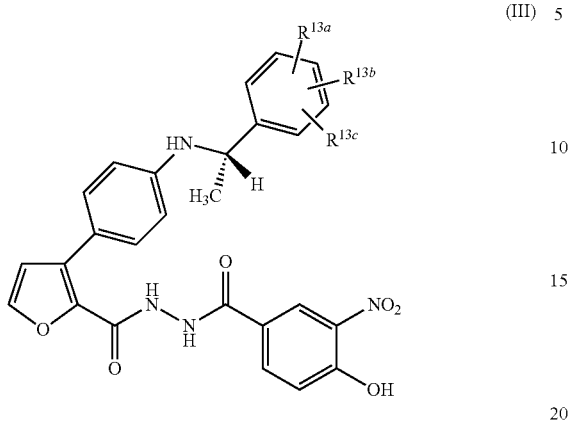

(III)

wherein $R^{13a}$, $R^{13b}$, and $R^{13c}$ are the same or different, and independently represent:
1: a hydrogen atom,
2: a halogen atom,
3: a $C_{1-4}$ alkyl group, which is optionally substituted with 1 to 3 fluorine atoms,
4: a $C_{1-4}$ alkoxy group, which is optionally substituted with 1 to 3 fluorine atoms, or
5: a $C_{1-4}$ alkylcarbonyl group, which is optionally substituted with $C_{1-4}$ alkoxy.

18. A method for treating a symptom and disease selected from the group consisting of hyperglycemia, abnormal glucose tolerance, insulin resistance syndrome, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, metabolic syndrome, and diabetic complications; the method comprising administering an effective amount of the compound according to claim 1 or a pharmaceutically acceptable salt thereof as an active ingredient into a patient in need thereof.

19. A method for treating a symptom and disease selected from the group consisting of hyperglycemia, abnormal glucose tolerance, insulin resistance syndrome, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, metabolic syndrome, and diabetic complications; the method comprising administering the compound according to claim 1 or a pharmaceutically acceptable salt thereof, and one drug selected from the drug group (A) below into a mammal in need thereof;
the drug group (A) consisting of insulin preparations, insulin resistance improving agents, α-glucosidase inhibitors, biguanides, insulin secretagogues, GLP-1, GLP-1 analogs, GLP-1 secretagogues, protein tyrosine phosphatase inhibitors, β3-agonists, DPPIV inhibitors, amyrin agonists, gluconeogenesis inhibitors, SGLT (sodium-glucose cotransporter) inhibitors, 11β-HSD1 inhibitors, adiponectin or adiponectin receptor agonists, leptin resistance improving drugs, somatostatin receptor agonists, AMPK activators, aldose reductase inhibitors, neurotrophic factors, PKC inhibitors, AGE inhibitors, active oxygen-eliminating agents, cerebral vasodilators, HMG-CoA reductase inhibitors, squalene synthetase inhibitors, ACAT inhibitors, cholesterol absorption inhibitors, angiotensin-converting enzyme inhibitors, angiotensin II antagonists, calcium antagonists, ACE/NEP inhibitors, β-blockers, α-blockers, αβ-blockers, renin inhibitors, aldosterone receptor antagonists, central anti-obesity drugs, pancreatic lipase inhibitors, peptide appetite suppressants, cholecystokinin agonists, xanthine derivatives, thiazide preparations, anti-aldosterone preparations, carbonic anhydrase inhibitors, chlorobenzene sulfonamide preparations, azosemido, isosorbide, ethacrynic acid, piretanide, bumetanide, and furosemide.

20. A method for producing a compound represented by Formula (II) or a pharmaceutically acceptable salt thereof:

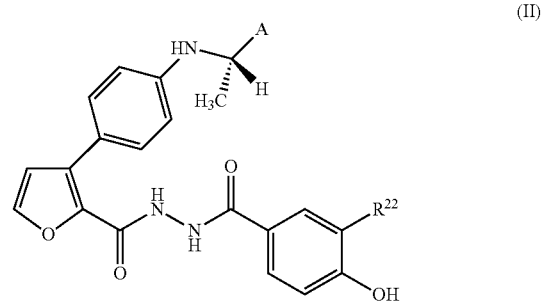

(II)

wherein A and $R^{22}$ are as defined in claim 1
the method comprising the step of reacting a compound represented by Formula (IV):

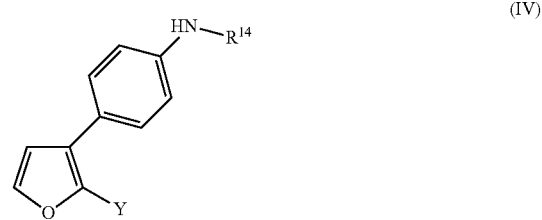

(IV)

wherein $R^{14}$ has the same meaning as the group

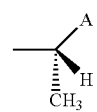

of formula (II) of claim 1, Y is a group: —COOR$^9$ or a group: —CONHNH$_2$, and R$^9$ is a hydrogen atom or a $C_{1-6}$ alkyl group, with a compound represented by Formula (K):

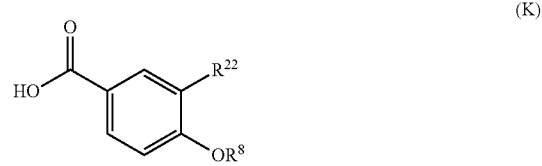

(K)

wherein $R^{22}$ is as defined above, and $R^8$ is a hydrogen atom, a $C_{1-4}$ alkyl group, a $C_{1-4}$ alkoxy $C_{1-4}$ alkyl group, a $C_{6-10}$ aryl group, a $C_{7-14}$ aralkyl group, or a $C_{1-4}$ alkylcarbonyl group; and, as necessary, converting the reaction product to a pharmaceutically acceptable salt.

21. The method according to claim 20, wherein Y is a group: —CONHNH$_2$.

22. The method according to claim 20 wherein Y is a group: —COOR$^9$, and a compound obtained by hydrazidation of the compound represented by Formula (IV) is reacted with the compound represented by Formula (K).

23. The method according to claim 21, further comprises the following steps 1 to 4 below, wherein the compound represented by Formula (IV) wherein Y is a group: —CONHNH$_2$ is obtained by the reaction of step 4:

Step 1: reacting a compound represented by Formula (A):)

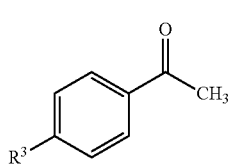

(A)

wherein R$^3$ is a halogen atom or a group: —N(R$_{14}$)(R$^5$)R$^5$ is a hydrogen atom, and R$^{14}$ is as defined above, with a compound represented by Formula (B):

HCOOR$^6$ (B)

wherein R$^6$ is a $C_{1-6}$ alkyl group, in the presence of a base, followed by a reaction in an alcohol solvent: R$^4$OH, wherein R$^4$ is a $C_{1-6}$ alkyl group, in the presence of an acid;

Step 2: reacting the compound obtained by the reaction of step 1 and represented by Formula (C):

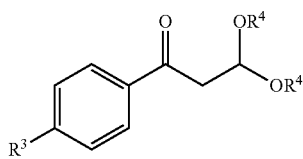

(C)

wherein R$^3$ and R$^4$ are as defined above, with a compound represented by Formula (E):

X$^1$—CH$_2$COOR$^7$ (E)

wherein X$^1$ is a halogen atom, and
R$^7$ is
  1: a $C_{1-6}$ alkyl group,
  2: a $C_{7-14}$ aralkyl group, which is optionally substituted with the same or different 1 to 3 groups selected from the group consisting of:
    (a) halogen,
    (b) methyl,
    (c) methoxy, and
    (e) nitro, or
  3: a $C_{6-10}$ arylcarbonyl $C_{1-4}$ alkyl group, which is substituted with the same or different 1 to 3 groups selected from the group consisting of:
    (a) halogen,
    (b) methyl, and
    (c) methoxy,
in the presence of a base;

Step 3: reacting the compound obtained by the reaction of step 2 and represented by Formula (F):

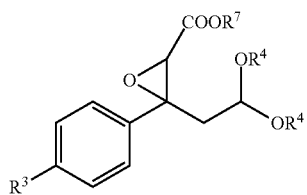

(F)

wherein R$^3$, R$^4$, and R$^7$ are as defined above, in the presence of an acid; and Step 4: reacting the compound obtained by the reaction of step 3 and represented by Formula (G):

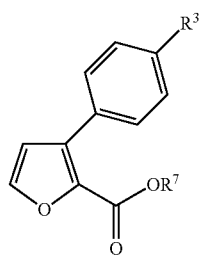

(G)

wherein R$^3$ and R$^7$ are as defined above, with
  (1) hydrazine monohydrate after a coupling reaction with a compound represented by Formula (H) below, when R$^3$ is a halogen atom:

R$^{14}$NH$_2$ (H)

wherein R$^{14}$ is as defined above, or with
  (2) hydrazine monohydrate, when R$^3$ is a group: —NH(R$^{14}$).

24. A compound represented by Formula (IV) below or a pharmaceutically acceptable salt thereof:

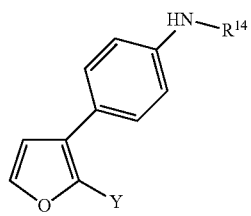

(IV)

wherein R$^{14}$
has the same meaning as the group

of formula (II) of claim 1
Y is a group: —COOR$^9$ or a group: —CONHNH$_2$; and
R$^9$ is a hydrogen atom or a $C_{1-6}$ alkyl group.

* * * * *